United States Patent
Yang et al.

(10) Patent No.: US 10,828,246 B2
(45) Date of Patent: Nov. 10, 2020

(54) EFFECTIVE HAIR STYLING COMPOSITIONS AND PROCESSES

(71) Applicant: NUtech Ventures, Lincoln, NE (US)

(72) Inventors: Yiqi Yang, Lincoln, NE (US); Helan Xu, Lincoln, NE (US); Kaili Song, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 15/284,336

(22) Filed: Oct. 3, 2016

(65) Prior Publication Data

US 2017/0095409 A1 Apr. 6, 2017

Related U.S. Application Data

(63) Continuation-in-part of application No. PCT/US2016/025696, filed on Apr. 1, 2016.

(60) Provisional application No. 62/142,586, filed on Apr. 3, 2015.

(51) Int. Cl.

| | | |
|---|---|---|
| *A61K 8/46* | (2006.01) | |
| *A61K 8/41* | (2006.01) | |
| *A61K 8/42* | (2006.01) | |
| *A45D 7/06* | (2006.01) | |
| *A61K 8/362* | (2006.01) | |
| *A61K 8/24* | (2006.01) | |
| *A61K 8/44* | (2006.01) | |
| *A61K 8/34* | (2006.01) | |
| *A61Q 5/06* | (2006.01) | |
| *A61K 8/37* | (2006.01) | |
| *A61Q 5/04* | (2006.01) | |

(52) U.S. Cl.
CPC ............... *A61K 8/46* (2013.01); *A45D 7/06* (2013.01); *A61K 8/24* (2013.01); *A61K 8/345* (2013.01); *A61K 8/362* (2013.01); *A61K 8/37* (2013.01); *A61K 8/41* (2013.01); *A61K 8/42* (2013.01); *A61K 8/44* (2013.01); *A61K 8/447* (2013.01); *A61K 8/463* (2013.01); *A61Q 5/04* (2013.01); *A61Q 5/06* (2013.01); *A61K 2800/80* (2013.01)

(58) Field of Classification Search
None
See application file for complete search history.

(56) References Cited

U.S. PATENT DOCUMENTS

| | | | |
|---|---|---|---|
| 2,929,794 A | 3/1960 | Simon et al. | |
| 4,299,817 A * | 11/1981 | Hannan, III | A61K 8/4946 424/70.13 |
| 6,093,412 A | 7/2000 | Philippe et al. | |
| 8,313,737 B2 | 11/2012 | Sabbagh et al. | |
| 2004/0115162 A1 | 6/2004 | Hoshino et al. | |
| 2006/0188460 A1 | 8/2006 | Ambrosen et al. | |
| 2006/0222618 A1 * | 10/2006 | Makino | A61K 8/447 424/70.51 |
| 2011/0021101 A1 | 1/2011 | Hawkins et al. | |
| 2011/0042816 A1 | 2/2011 | Fujiwara et al. | |
| 2011/0086567 A1 | 4/2011 | Hawkins et al. | |
| 2011/0189119 A1 * | 8/2011 | Jin | A61K 8/44 424/70.51 |
| 2011/0311868 A1 | 12/2011 | Sano et al. | |
| 2013/0129646 A1 | 5/2013 | Vielhaber et al. | |
| 2014/0179803 A1 | 6/2014 | Van Den Broek et al. | |
| 2015/0297496 A1 * | 10/2015 | Kroon | A61Q 5/06 424/54 |

FOREIGN PATENT DOCUMENTS

| | | | |
|---|---|---|---|
| EP | 1046390 A1 * | 10/2000 | |
| WO | WO 2000/029662 | 5/2000 | |
| WO | WO 2015/168662 | 11/2015 | |

OTHER PUBLICATIONS

The Good Scents Company web page for 2-(2-aminoethoxy)ethanol (May 6, 2013). Retrieved from <www.thegoodscentscompany.com/data/rw1167611.html>.*
Google publication date web page for the the Good Scents Company web page for 2-(2-aminoethoxy)ethanol (Jan. 22, 2018).*
Boga et al., "Formaldehyde replacement with glyoxylic acid in semipermanent hair straightening: a new and multidisciplinary investigation," International Journal of Cosmetic Science, 2014, 36: 459.
Bryson et al., "Cortical cell types and intermediate filament arrangements correlate with fiber curvature in Japanese human hair," Journal of Structural Biology, 2009, 166: 46-58.
Galiotte et al., "Assessment of Occupational Genotoxic Risk among Brazilian Hairdressers," Annals of Occupational Hygiene, 2008, 52: 645.
Hampton, "Toxic Hair Products," JAMA, 2011, 305: 2056.
International Search Report and Written Opinion in International Application No. PCT/US2016/025696, dated Jul. 1, 2016, 20 pages.
Khumalo et al., "Hair fashion trends and formaldehyde health risks," SAMJ: South African Medical Journal, Dec. 2011, 101: 872.
Knorst and Lorenzini, "Exposure of Hairdressers to Formaldehyde: Short and Long-Term Effects on Symptoms and Lung Function," Am J Respir Crit Care Med, 2013, 187: A3673. Maneli et al., "Elevated formaldehyde concentration in "Brazilian keratin type" hair-straightening products: A cross-sectional study," Journal of the American Academy of Dermatology, Feb. 2014, 70: 276.
Mottram et al., "Food chemistry: Acrylamide is formed in the Maillard reaction," Nature, Oct. 2002, 419: 448.

(Continued)

*Primary Examiner* — Patricia Duffy
*Assistant Examiner* — Garen Gotfredson
(74) *Attorney, Agent, or Firm* — Fish & Richardson P.C.

(57) ABSTRACT

This disclosure relates to hair styling compositions and processes, and more particularly to compositions for disentangling or crosslinking hair that are useful in hair styling processes.

24 Claims, 13 Drawing Sheets

(56) References Cited

OTHER PUBLICATIONS

Thibaut et al., "Human hair keratin network and curvature," International Journal of Dermatology, 2007, 46: 7.

* cited by examiner

EFFECTIVE HAIR STYLING COMPOSITIONS AND PROCESSES

CROSS-REFERENCE TO RELATED APPLICATIONS

This application is a continuation-in-part of International Application No. PCT/US2016/025696, filed Apr. 4, 2016, which claims the benefit of U.S. Provisional Application Ser. No. 62/142,586, filed Apr. 3, 2015, the disclosure of each of which is incorporated herein by reference in its entirety.

FEDERALLY SPONSORED RESEARCH OR DEVELOPMENT

This invention was made with Government support under Grant Nos. 2013-31200-06031, 2014-31200-06031, and 2015-31200-06031 awarded by the United States Department of Agriculture and the National Institute of Food and Agriculture. The Government has certain rights in the invention.

TECHNICAL FIELD

This disclosure relates to compositions for hair styling and methods of using the same.

BACKGROUND

Morphology of hair is mainly determined by distribution of two types of cells with different hydrophilicity. For both cells, hard α-keratin molecules (intermediate filaments, IFs) are the basic building units embedded in matrix proteins. The relatively hydrophilic cells contain less disulfide cross-linking and IFs mainly in helical conformation, while the relatively hydrophobic cells contain higher contents of disulfide bonds and IFs in both helix and parallel arrangements (see, e.g., Bryson et al., *Journal of Structural Biology*, 2009, 166, 46). Curly hair has bilateral distribution of the two cell types, while straight hair has annular and even distribution of them (see, e.g., Thibaut et al., *International Journal of Dermatology*, 2007, 46, 7). In curly hair, the relatively hydrophilic cells that swell more upon water uptake, mostly locate at the convex, while the relatively hydrophobic cells that swell less mainly distribute at the concave. In straight hair, the cells swell uniformly and thus typically maintain the straightness of hair in wet conditions.

SUMMARY

The present application provides, inter alia, a composition comprising:
(i) one or more independently selected reducing agents; and
(ii) one or more independently selected disentangling agents;
wherein each of the one or more independently selected disentangling agents is selected from the group consisting of an alkanolamine, an amine, an amide, an alcohol, an amino acid, a surfactant, an anhydride, a guanidinium salt, an ester, and combinations thereof.

In some embodiments, each of the one or more independently selected reducing agents is selected from the group consisting of a thiol compound, a sulfite compound, a bisulfite compound, a sulfide compound, a bisulfide compound, and tris(2-carboxy ethyl)phosphine (TCEP), or salt forms of any of the foregoing.

In some embodiments, at least one of the one or more independently selected reducing agents is selected from the group consisting of 2,3 dihydroxybutane-1,4-dithiol (DTT), 2,3 dihydroxybutane-1,4-dithiol (DTE), mercaptoethanol, thioglycolate, cysteine, mercaptoethanol, dithiothreitol, and glutathione. In some embodiments, at least one of the one or more independently selected reducing agents is cysteine.

In some embodiments, at least one of the one or more independently selected disentangling agents is an alkanolamine. In some embodiments, at least one of the one or more independently selected alkanolamines comprise 1 to 20 carbons. In some embodiments, at least one of the one or more independently selected alkanolamines is selected from the group consisting of ethanolamine, triethanolamine, heptaminol, propanolamine, 2-(2-aminoethoxy)ethanol, and 2-amino-4-octadecene-1,3-diol. In some embodiments, at least one of the one or more independently selected alkanolamines is 2-(2-aminoethoxy)ethanol.

In some embodiments, at least one of the one or more independently selected disentangling agents is an amine. In some embodiments, at least one of the one or more independently selected amines is selected from the group consisting of mono($C_{1-20}$ alkyl)amine, di($C_{1-20}$ alkyl)amine, tri($C_{1-20}$ alkyl)amine, wherein each $C_{1-20}$ alkyl group may be optionally substituted. In some embodiments, at least one of the one or more independently selected amines is selected from the group consisting of propylamine, ethylenediamine, isopropylamine, methylamine, dimethylamine, and trimethylamine.

In some embodiments, at least one of the one or more independently selected disentangling agents is an amide. In some embodiments, at least one of the one or more independently selected amides comprise 1 to 20 carbon atoms. In some embodiments, at least one of the one or more independently selected amides is selected from the group consisting of dimethylacetamide, acrylamide, and carbamide. In some embodiments, at least one of the one or more independently selected amides is dimethylacetamide.

In some embodiments, at least one of the one or more independently selected disentangling agents is an alcohol. In some embodiments, at least one of the one or more independently selected alcohol is a monohydric alcohol or a polyhydric alcohol, each of which comprise 1 to 20 carbon atoms. In some embodiments, at least one of the one or more independently selected monohydric alcohols is selected from the group consisting of ethanol, isopropanol, and n-butanol. In some embodiments, at least one of the one or more independently selected polyhydric alcohols is selected from the group consisting of ethylene glycol, propylene glycol, glycerol, erythritol, xylitol, mannitol, and volemitol.

In some embodiments, at least one of the one or more independently selected disentangling agents is a surfactant. In some embodiments, at least one of the one or more independently selected surfactants is an anionic surfactant. In some embodiments, at least one of the one or more independently selected anionic surfactants is selected from the group consisting of sodium dodecyl sulfate, sodium dodecyl benzenesulfonate, sodium lauroyl sarcosinate, perfluorobutanesulfonic acid, and ammonium lauryl sulfate. In some embodiments, at least one of the one or more independently selected surfactants is a cationic surfactant. In some embodiments, at least one of the one or more independently selected cationic surfactants is selected from the group consisting of benzalkonium chloride, cetrimonium bromide, and tetramethylammonium hydroxide. In some embodiments, at least one of the one or more independently selected surfactants is a non-ionic surfactant. In some embodiments, at least one of the one or more independently selected non-ionic surfactants is selected from the group consisting of triton X-100, polysorbate 80, polysorbate 20, and decyl glucoside.

In some embodiments, at least one of the one or more independently selected disentangling agents is an anhydride. In some embodiments, at least one of the one or more independently selected anhydrides comprise 2 to 20 carbon atoms. In some embodiments, at least one of the one or more independently selected anhydrides is selected from the group consisting of acetic anhydride, maleic anhydride, butyric anhydride, succinic anhydride, and methylsuccinic anhydride.

In some embodiments, at least one of the one or more independently selected disentangling agents is a guanidinium salt. In some embodiments, at least one of the one or more independently selected guanidinium salts is a guanidinium halide. In some embodiments, at least one of the one or more independently selected guanidinium halides is guanidinium chloride.

In some embodiments, at least one of the one or more independently selected disentangling agents is an ester. In some embodiments, at least one of the one or more independently selected esters comprise 2 to 20 carbon atoms. In some embodiments, at least one of the one or more independently selected esters is ethyl acetate.

In some embodiments, the composition comprises one reducing agent and one disentangling agent.

In some embodiments, the composition further comprises a solvent. In some embodiments, the solvent comprises water.

In some embodiments, the total concentration of the one or more independently selected reducing agents is from about 0.05 mol/L to about 2 mol/L. In some embodiments, the total concentration of the one or more independently selected reducing agents is from about 0.1 mol/L to about 1 mol/L. In some embodiments, the total concentration of the one or more independently selected disentangling agents is from about 0.5 mol/L to about 11 mol/L. In some embodiments, the total concentration of the one or more independently selected disentangling agents is from about 0.5 mol/L to about 10 mol/L. In some embodiments, the total concentration of the one or more independently selected disentangling agents is from about 0.5 mol/L to about 5 mol/L.

In some embodiments, the composition comprises:
(i) a reducing agent; and
(ii) a disentangling agent;
wherein the reducing agent comprises cysteine and the disentangling agent is selected from the group consisting of 2-(2-aminoethoxy)ethanol, sodium dodecyl sulfate, dimethylacetamide, ethyl acetate, and mixtures of two or more thereof.

In some embodiments, the composition comprises:
(i) a reducing agent; and
(ii) a disentangling agent;
wherein the reducing agent is cysteine and the disentangling agent is 2-(2-aminoethoxy)ethanol.

In some embodiments, the composition comprises:
(i) a reducing agent; and
(ii) a disentangling agent;
wherein the reducing agent is cysteine and the disentangling agent is sodium dodecyl sulfate.

In some embodiments, the composition comprises:
(i) a reducing agent; and
(ii) a disentangling agent;
wherein the reducing agent is cysteine and the disentangling agent is dimethylacetamide.

In some embodiments, the composition comprises:
(i) a reducing agent; and
(ii) a disentangling agent;
wherein the reducing agent is cysteine and the disentangling agent is ethyl acetate. In some embodiments, the composition further comprises a solvent. In some embodiments, the solvent comprises water.

In some embodiments, the total concentration of the reducing agent is from about 0.05 mol/L to about 2 mol/L. In some embodiments, the total concentration of the reducing agent is from about 0.1 mol/L to about 1 mol/L. In some embodiments, the total concentration of the disentangling agent is from about 0.5 mol/L to about 11 mol/L. In some embodiments, the total concentration of the disentangling agent is from about 0.5 mol/L to about 10 mol/L. In some embodiments, the total concentration of the disentangling agent is from about 0.5 mol/L to about 5 mol/L.

In some embodiments, the pH of the composition is from about 5 to about 12. In some embodiments, the pH of the composition is from about 6 to about 9.

In some embodiments, the composition further comprises a base. In some embodiments, the base is sodium hydroxide.

The present application further provides a composition, comprising:
(i) one or more independently selected polycarboxylic acids;
(ii) one or more independently selected alkali metal hypophosphites; and
(iii) one or more independently selected crosslinking agents;
wherein each of the one or more independently selected crosslinking agents is selected from the group consisting of a carbohydrate, an amino acid, a peptide, an oligopeptide, a protein hydrolysate, an alkanolamine, an alcohol, and combinations thereof.

In some embodiments, at least one of the one or more independently selected polycarboxylic acids is citric acid.

In some embodiments, at least one of the one or more independently selected alkali metal hypophosphites is selected from the group consisting of lithium hypophosphite, sodium hypophosphite, and potassium hypophosphite. In some embodiments, at least one of the one or more independently selected alkali metal hypophosphites is sodium hypophosphite.

In some embodiments, at least one of the one or more independently selected crosslinking agents is a carbohydrate. In some embodiments, at least one of the one or more independently selected carbohydrates is a monosaccharide. In some embodiments, at least one of the one or more independently selected monosaccharides is selected from the group consisting of glucose, fructose, and galactose. In some embodiments, at least one of the one or more independently selected carbohydrates is a disaccharide. In some embodiments, at least one of the one or more independently selected disaccharides is selected from the group consisting of sucrose, lactulose, maltose, and cellobiose. In some embodiments, at least one of the one or more independently selected carbohydrates is a polysaccharide. In some embodiments, at least one of the one or more independently selected polysaccharides is selected from the group consisting of starch, cellulose, and pectin.

In some embodiments, at least one of the one or more independently selected crosslinking agents is an amino acid. In some embodiments, at least one of the one or more independently selected amino acids is a natural amino acid. In some embodiments, at least one of the one or more independently selected natural amino acids is selected from the group consisting of lysine, arginine, histidine, serine, and threonine. In some embodiments, at least one of the one or more independently selected natural amino acids is lysine.

In some embodiments, at least one of the one or more independently selected crosslinking agents is selected from the group consisting of a peptide, an oligopeptide, and a protein hydrolysate.

In some embodiments, at least one of the one or more independently selected crosslinking agents is an alkanolamine. In some embodiments, at least one of the one or more independently selected alkanolamines comprise 1 to 20 carbon atoms. In some embodiments, at least one of the one or more independently selected alkanolamines is selected from the group consisting of ethanolamine, heptaminol, propanolamine, 2-(2-aminoethoxy)ethanol, and 2-amino-4-octadecene-1,3-diol. In some embodiments, at least one of the one or more independently selected alkanolamines is 2-(2-aminoethoxy)ethanol.

In some embodiments, at least one of the one or more independently selected crosslinking agents is an alcohol. In some embodiments, at least one of the one or more independently selected alcohols is a polyhydric alcohol comprising 1 to 20 carbon atoms. In some embodiments, at least one of the one or more independently selected polyhydric alcohols is selected from the group consisting of ethylene glycol, propylene glycol, glycerol, erythritol, xylitol, mannitol, and volemitol. In some embodiments, at least one of the one or more independently selected polyhydric alcohols is glycerol or mannitol.

In some embodiments, the composition further comprises a solvent. In some embodiments, the solvent comprises water.

In some embodiments, the composition comprises from about 0.1 mol/L to about 1.5 mol/L of the polycarboxylic acid. In some embodiments, the composition comprises from about 0.75 mol/L to about 1.2 mol/L of the polycarboxylic acid.

In some embodiments, the composition comprises about 0.5 mol/L to about 1.5 mol/L of the alkali metal hypophosphite. In some embodiments, the composition comprises from about 0.75 mol/L to about 1.2 mol/L of the alkali metal hypophosphite.

In some embodiments, the composition comprises from about 0.1 mol/L to about 10 mol/L of the crosslinking agent. In some embodiments, the composition comprises from about 0.1 mol/L to about 3 mol/L of the crosslinking agent. In some embodiments, the composition comprises from about 0.5 mol/L to about 3 mol/L of the crosslinking agent. In some embodiments, the composition comprises from about 0.5 mol/L to about 1.2 mol/L of the crosslinking agent. In some embodiments, the composition comprises 0.5 mol/L to about 1.1 mol/L of the crosslinking agent.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L of a crosslinking agent;
wherein the crosslinking agent is selected from the group consisting of 2-(2-aminoethoxy)ethanol, lysine, glycerol, and mannitol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L a crosslinking agent;
wherein the crosslinking agent is 2-(2-aminoethoxy)ethanol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L a crosslinking agent;
wherein the crosslinking agent is lysine.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L a crosslinking agent;
wherein the crosslinking agent is glycerol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L a crosslinking agent;
wherein the crosslinking agent is mannitol.

In some embodiments, the composition further comprises a solvent. In some embodiments, the solvent comprises water.

The present application further provides a method of styling hair, the method comprising:
(i) contacting the hair with a disentangling composition provided herein;
(ii) optionally heating the hair; and
(iii) shaping the hair to a specific style.

In some embodiments, the optional heating of step (ii) is performed at from about 20° C. to about 90° C. In some embodiments, the optional heating of step (ii) is performed at from about 45° C. to about 55° C.

In some embodiments, the shaping of step (iii) is performed using a styling tool.

In some embodiments, the styling tool is selected from the group consisting of a heating tool, a shaping tool, and a heating and shaping tool. In some embodiments, the styling tool is a flat iron or a curling iron.

In some embodiments, the method further comprises rinsing and drying the hair. In some embodiments, the rinsing and drying is performed after waiting a sufficient time after the shaping of step (iii). In some embodiments, the sufficient time is from about 1 to about 90 minutes. In some embodiments, the sufficient time is from about 20 to about 45 minutes. In some embodiments, the sufficient time is from about 20 to 35 minutes.

In some embodiments, the method of styling hair comprises straightening the hair or curling the hair.

The present application further provides a method of styling hair, comprising contacting the hair with a crosslinking composition provided herein.

In some embodiments, the contacting further comprises waiting a time sufficient to allow crosslinking. In some embodiments, the waiting is from about 1 minute to about 30 minutes. In some embodiments, the waiting is from about 1 minute to about 15 minutes. In some embodiments, the waiting is from about 1 minute to about 5 minutes.

In some embodiments, the contacting further comprises heating the hair. In some embodiments, the heating is performed at from about 20° C. to about 250° C. In some embodiments, the heating is performed at from about 100° C. to about 200° C. In some embodiments, the heating is performed at about 180° C.

In some embodiments, the method further comprises rinsing and drying the hair In some embodiments, the rinsing and drying is performed at from about 30 minutes to about 48 hours after the contacting. In some embodiments, the rinsing and drying is performed at from about 18 hours to about 48 hours after the contacting. In some embodiments, the rinsing and drying is performed at about 24 hours after the contacting.

In some embodiments, the method of styling hair comprises straightening the hair or curling the hair.

The present application further provides a method of styling hair, comprising:

(i) contacting the hair with a composition of any one of claims 1 to 59;

(ii) optionally heating the hair;

(iii) shaping the hair to a specific style;

(iv) contacting the hair with a composition of any one of claims 60 to 101; and (v) waiting a time sufficient to allow crosslinking.

In some embodiments, the optional heating of step (ii) is performed at from about 20° C. to about 90° C. In some embodiments, the optional heating of step (ii) is performed at from about 45° C. to about 55° C. In some embodiments, the shaping of step (iii) is performed using a styling tool. In some embodiments, the styling tool is selected from the group consisting of a heating tool, a shaping tool, and a heating and shaping tool. In some embodiments, the styling tool is a flat iron or a curling iron. In some embodiments, the shaping of step (iii) comprises straightening the hair.

In some embodiments, the method further comprises rinsing and drying the hair after the shaping of step (iii) and before contacting of step (iv). In some embodiments, the rinsing and drying is performed after waiting a sufficient time after the shaping of step (iii). In some embodiments, the sufficient time is from about 1 to about 90 minutes. In some embodiments, the sufficient time is from about 20 to about 45 minutes. In some embodiments, the sufficient time is from about 20 to 35 minutes.

In some embodiments, the waiting of step (v) is from about 1 minute to about 30 minutes. In some embodiments, the waiting of step (v) is from about 1 minute to about 15 minutes. In some embodiments, the waiting of step (v) is from about 1 minute to about 5 minutes. In some embodiments, the waiting of step (v) further comprises heating the hair.

In some embodiments, the heating is performed at from about 50° C. to about 250° C. In some embodiments, the heating is performed at from about 100° C. to about 200° C.

In some embodiments, the heating is performed at about 180° C.

In some embodiments, the method further comprises rinsing and drying the hair after step (v). In some embodiments, the rinsing and drying is performed at from about 30 minutes to about 48 hours after step (v). In some embodiments, the rinsing and drying is performed at from about 18 hours to about 48 hours after step (v). In some embodiments, the rinsing and drying is performed at about 24 hours after step (v).

In some embodiments, the method of styling hair comprises straightening the hair or curling the hair.

The present application further provides a kit, comprising:

(i) one or more of the independently selected reducing agents provided herein;

(ii) one or more of the independently selected disentangling agents provided herein;

(iii) one or more of the independently selected polycarboxylic acids provided herein;

(iv) one or more of the independently selected alkali metal hypophosphites provided herein;

(v) one or more of the independently selected crosslinking agents provided herein; and (vi) instructions for using the kit.

In some embodiments, the instructions describe a process for mixing the one or more independently selected reducing agents and one or more independently selected disentangling agents to form the composition provided herein.

In some embodiments, the instructions describe a process for mixing the one or more independently selected polycarboxylic acids, the one or more independently selected alkali metal hypophosphites, and the one or more independently selected crosslinking agents to form the composition provided herein.

In some embodiments, the instructions describe a process for performing a method of styling hair provided herein.

In some embodiments, the kit comprises:

(i) a disentangling composition provided herein;

(ii) a crosslinking composition provided herein; and (iii) instructions for using the kit.

In some embodiments, the instructions describe a process for performing a method of hair styling provided herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1A:
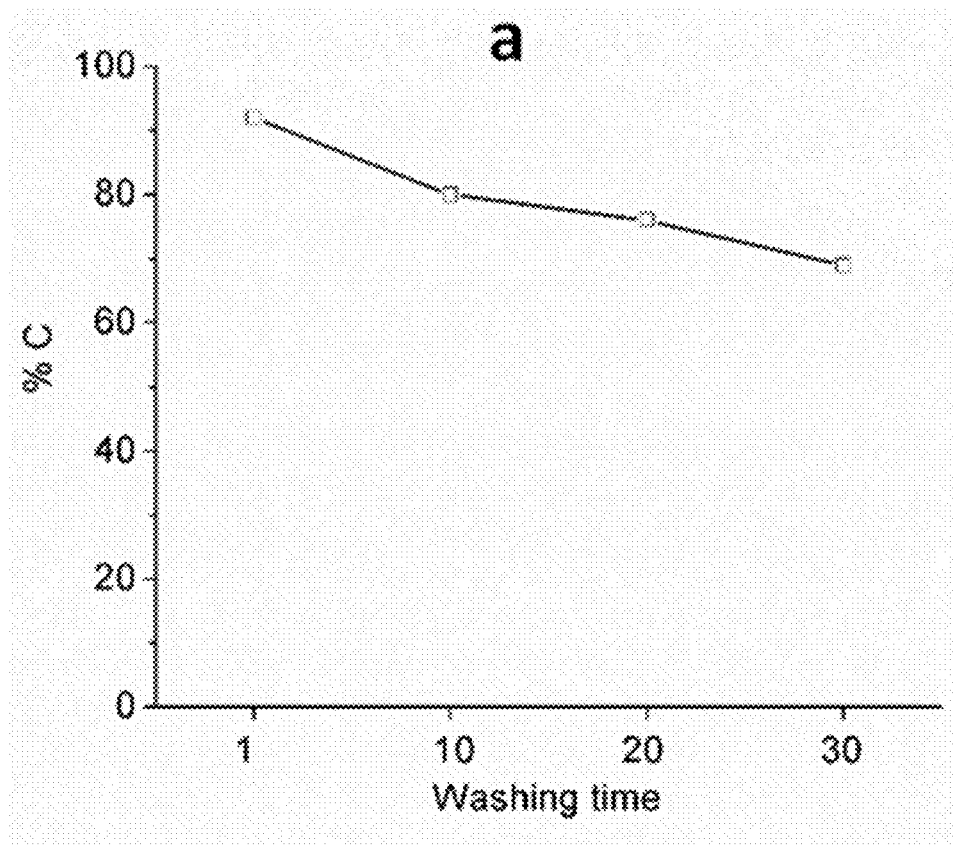
FIG. 1a shows the effect of washing time on the % C of the straightened curly hair using 2-(2-aminoethoxy)ethanol as the dis-entangling agent and crosslinking booster.

The present application provides compositions and methods for hair styling, including straightening and curling. The methods can include dis-assembling secondary and tertiary structures of keratins to promote intermolecular diffusion, followed by booster assisted chemical crosslinking to solidify the re-organized molecular structures. Due to the similarity between molecular structures of human hair and animal hair, the compositions and methods provided herein can be further applied in pet care or pet grooming as safe and effective compositions and methods useful for obtaining new durable hair styles for animals (e.g., dogs and cats).

To achieve long-lasting straightening or curling effects of hair, the first step can include substantially disrupting the original molecular stability of the hair by reducing inter- and intra-molecular friction to facilitate easy slippage and diffusion of keratin polypeptides. The high intermolecular friction of hair can be attributed to the physical intertwining of the helical keratin polypeptides as well as high degree of chemical crosslinking that fixes the hair's conformations. Therefore, both removal of chemical crosslinking and untwining of the entangled helical polypeptides can be used to relax the hair and may function as a first step of hair styling.

Despite their high crosslinking efficaciousness, aldehydes, especially formaldehyde, are strictly limited for their use in hair styling products due to their carcinogenicity and toxicity (see, e.g., Hampton, *JAMA,* 2011, 305, 2056; Boga et al., *International Journal of Cosmetic Science,* 2014, 36, 459; Galiotte et al., *Annals of Occupational Hygeine,* 2008, 52, 645). Moreover, a Maillard reaction can occur between aldehydes and proteins; this reaction has been shown to produce acrylamide, a probable human carcinogen (Mottram et al., *Nature,* 2002, 419, 448). However, lacking cost-effective substitutes, formaldehyde, glyoxal, glutaraldehyde and other aldehydes are either still in use or proposed to be used in hair styling products. Furthermore, even for the potent formaldehyde, only at concentrations as high as 5% to 12% could satisfactory straightening or curling effects be achieved (Lorenzini et al., *Am J Respir Crit Care Med,* 2013, 187, A3673; Maneli et al., *Journal of the American Academy of Dermatology,* 2014, 70, 276). If the concentrations are reduced to about 1%, which still exceeded the officially allowed amount (0.2%), the solution could only reduce the frizziness of hair (Khumalo et al., *SAMJ: South African Medical Journal,* 2011, 101, 872). The necessity of using high concentrations also reflects the deficiency in the previous hair relaxation step, as the high internal stress due to the un-interrupted entangled helices of keratin polypeptides can only be compensated by re-creation of strong inter- and intra-molecular interaction via extensive crosslinking.

The present application provides compositions useful for hair treatment, focusing on effectively altering the helical conformation of keratin and promoting forced diffusion of the keratin polypeptides. Non-toxic de-crosslinking, disentangling agents and their combinations are introduced to sufficiently de-assemble (i.e., alter) the helical conformation of hair and force the hair IFs to diffuse at the boundaries of hydrophobic and hydrophilic cell types.

The present application further provides compositions that promote non-toxic crosslinking of protein using less potent polycarboxylic acids. For example, different types of crosslinking boosters and their combinations are used to assist crosslinking using non-toxic polycarboxylic acids to achieve effective fixation of the hair IFs at new positions.

Definitions

The following abbreviations may be used herein: % C (degree of straightening); dimethylacetamide (DMAc); % E (degree of curling); IF(s) (intermediate filament(s)); L (liter); $L_0$ (length of hair without tension); $L_s$ (length of completely straightened hair); min. (minutes(s)); mm (millimeter(s)); $N_0$ (number of circles per unit length); $N_c$ (theoretical number of circles of hair wound on a rod per unit length without tension before heating); sodium dodecyl sulfate (SDS); sodium hypophosphite (SHP).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, $C_{1-10}$, $C_{1-20}$, and the like.

As used herein, the term "alkyl", employed alone or in combination with other terms, refers to a saturated hydrocarbon group that may be straight-chain or branched. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl moiety contains from 1 to 20 carbon atoms, from 1 to 15 carbon atoms, from 1 to 10 carbon atoms, 1 to 8 carbon atoms, or from 1 to 6 carbon atoms.

As used herein, "alkenyl" refers to an alkyl group having one or more double carbon-carbon bonds. Example alkenyl groups include, but are not limited to, ethenyl, n-propenyl, isopropenyl, n-butenyl, sec-butenyl, and the like. In some embodiments, the alkenyl moiety contains from 1 to 20 carbon atoms, from 1 to 15 carbon atoms, from 1 to 10 carbon atoms, 1 to 8 carbon atoms, or from 1 to 6 carbon atoms.

As used herein, "alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains from 1 to 20 carbon atoms, from 1 to 15 carbon atoms, from 1 to 10 carbon atoms, 1 to 8 carbon atoms, or from 1 to 6 carbon atoms.

As used herein, the term "alkali metal hypophosphite" refers to a group of formula $MH_2PO_2$, where M is an alkali metal (e.g., lithium, sodium, potassium, and the like).

As used herein, the term "alkanolamine" refers to a compound of formula $HO—R—NH_3$, wherein R represents a linear or branched alkyl, alkenyl, or alkynyl group, a cycloalkyl group, an aryl group, a heterocyclic group, or a heteroaryl group. Example alkanolamines include, but are not limited to, methanolamine, ethanolamine, triethanolamine, iso-propanolamine, n-butanolamine, iso-butanolamine, tert-butanolamine, heptaminol, propanolamine, 2-(2-aminoethoxy)ethanol, 2-amino-4-octadecene-1,3-diol, and the like.

As used herein, the term "alcohol" refers to a compound of formula R—OH, wherein R represents a linear or branched alkyl, alkenyl, or alkynyl group, a cycloalkyl group, an aryl group, a heterocyclic group, or a heteroaryl group. In some embodiments, the alcohol is a monohydric alcohol (e.g., the alcohol comprises 1 OH group). Example monohydric alcohols include, but are not limited to, methanol, ethanol, n-propanol, isopropanol, n-butanol, isobutanol, tert-butanol, pentanol, octanol, decanol, and the like. In some embodiments, the alcohol is a polyhydric alcohol (e.g., the alcohol comprises more than 1 OH group). Example polyhydric alcohols include, but are not limited to ethylene glycol, propylene glycol, glycerol, erythritol, xylitol, mannitol, 1,2,3,4-butanetetrol, volemitol, threitol, arabitol, ribitol, sorbitol, galactitol, fucitol, iditol, inositol, isomalt, maltitol, lactitol, maltotriitol, and the like.

As used herein, the term "amine" refers to a mono-substituted amine group (i.e., primary amine), di-substituted amine group (i.e., secondary amine), or a tri-substituted amine group (i.e., tertiary amine). Example mono-substituted amines include, but are not limited to, methylamine, ethylamine, n-propylamine, isopropylamine, n-butylamine, isobutylamine, tert-butylamine, ethylenediamine, and the like. Example di-substituted amine bases include, but are not limited to, dimethylamine, diethylamine, dipropylamine, dibutylamine, pyrrolidine, piperidine, azepane, morpholine, and the like. Example tertiary amine bases include, but are not limited to, trimethylamine, triethylamine, tri-n-propylamine, triisopropylamine, tri-n-butylamine, tri-tert-butylamine, N,N-dimethylethanamine, N-ethyl-N-methylpropan-2-amine, N-ethyl-N-isopropylpropan-2-amine, N-methylmorpholine, and the like.

As used herein, the term "amide" refers to a compound of formula $RC(=O)NR'R''$, wherein R, R', and R'' each independently represent a hydrogen, a linear or branched alkyl, alkenyl, or alkynyl group, a cycloalkyl group, an aryl group, a heterocyclic group, or a heteroaryl group. Alternatively, R represents an unsubstituted amine group ($—NH_2$), a mono-substituted amine group (—NHR'), or a di-substituted amine group (—NR'R''), wherein R' and R'' are defined according to the definitions provided herein. Example amides include, but are not limited to, formamide, acetamide, carbamide, dimethylformamide (DMF), acetamide, dimethylacetamide (DMAc), N-methylformamide, N-vinylacetamide, 2-pyrrolidone, N-methyl-2-pyrrolidone, N-vinylpyrrolidone, and the like.

As used herein the term "anhydride" refers to a compound of formula $R—C(=O)—O—C(=O)R'$, wherein R and R' are each independently a hydrogen, a linear or branched alkyl, alkenyl, or alkynyl group, a cycloalkyl group, an aryl group, a heterocyclic group, or a heteroaryl group. Alternatively, R and R', together with the atoms to which they are attached, may come together to form a 5 to 20 membered heterocyclic ring. Example anhydrides include, but are not limited to, acetic anhydride, maleic anhydride, propionic anhydride, butyric anhydride, malonic anhydride, succinic anhydride, and methylsuccinic anhydride, and the like.

As used herein, the term "carboxylic acid" refers to a compound of formula $RC(=O)OH$, where R represents a hydrogen, a linear or branched alkyl, alkenyl, or alkynyl group, a cycloalkyl group, an aryl group, a heterocyclic group, or a heteroaryl group. Example carboxylic acids include, but are not limited to, formic acid, acetic acid, propionic acid, caprylic acid, capric acid, lauric acid, and the like.

As used herein, the term "polycarboxylic acid" refers to compounds having more than one $—C(=O)OH$ moiety. Example polycarboxylic acids include, but are not limited to, citric acid, butanetetracarboxylic acid (BTCA), oxalic acid, malonic acid, maleic acid, succinic acid, aconitic acid, adipic acid, pimelic acid, suberic acid, glutaric acid, azeliaic acid, sebacic acid, and the like.

As used herein, the term "carbohydrate" refers to linear, cyclic, and oxidized saccharides. It is understood that the term carbohydrate refers to monosaccharides, disaccharides, oligosaccharides, and polysaccharides, each of which may be optionally oxidized (e.g., an oxidized monosaccharide, an oxidized disaccharide, an oxidized oligosaccharide, an oxidized polysaccharide, and the like). Example monosaccharides include, but are not limited to glucose, fructose, galactose, ribose, deoxyribose, mannose, tagatose, and the like. Example disaccharides include, but are not limited to sucrose, lactose, lactulose, maltose, cellobiose, trehalose, and the like. Example polysaccharides include, but are not limited to, starch, cellulose, pectin, dextran, agarose, amylopectin, amylose, fructan, glucan, and the like. Example monosaccharides useful for preparing oxidized monosaccharides include, but are not limited to, glucose, fructose, galactose, glucosamine, dihydroxyacetone, erythrose, threose, erythrulose, arabinose, lyxose, ribose, xylose, ribulose, xylulose, allose, altrose, mannose, gulose, idose, talose, psicose, sorbose, tagatose, sedoheptulose, rhamnose, mannoheptulose, and the like. Example disaccharides useful for preparing oxidized disaccharides include, but are not limited to, sucrose, lactose, maltose, trehalose, lactulose, cellobiose, chitobiose, kojibiose, nigerose, isomaltose, sophorose, laminaribiose, gentiobiose, turanose, maltulose, palatinose, gentiobiulose, rutinulose, xylobiose, mannobiose, melibiose, melibiulose, rutinose, and the like. Example oligosaccharides useful for preparing oxidized oligosaccharides include, but are not limited to, isomaltotriose, nigerotriose, maltotriose, melezitose, maltotriulose, kestose, lychnose, maltotetraose, nigerotetraose, nystose, sesamose, starchyose, raffinose, fructo-oligosaccharide, galactooligosaccharide, mannan oligosaccharide, Brucella M Tetrasaccharide, thiooligosaccharide, and the like. Example polysaccharides useful for preparing oxidized polysaccharides include, but are not limited to, cellulose, amylose, amylopectin, glycogen, chitin, chitosan, alginate, callose, carrageenan, agar, fucoidan, laminarin, curdlan, xylan, chrysolaminarin, arabinoxylan, amylose, mannan, fucoidan, galactomannan, arabinoxylan, amylopectin, pectin, xanthan gum, welan gum, gellan gum, diutan gum, pullulan, and the like. Oxidized saccharides may be prepared, for example, by reacting a saccharide (e.g., a monosaccharide, disaccharide, oligosaccharide, polysaccharide, and the like) in the presence of an oxidizing agent under standard oxidation conditions known in the art (e.g., reaction with $Ag^+$ in $NH_3/H_2O$; reaction with $Br_2$ in H₂O; reaction with HNO₃; and the like). In some embodiments, the carbohydrate is selected from the group consisting of a linear and cyclic saccharide.

As used herein, the term "crosslinking agent" refers to a compound that effectively promotes disulfide crosslinking in a keratin containing substance (e.g., a compound that promotes disulfide crosslinking in hair).

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have from 3 to 20 ring-forming carbons, for example, from 3 to 20, from 3 to 15, from 3 to 10, from 3 to 8, or from 3 to 6. Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, the term "disentangling agent" refers to any compound that effectively alters the helical conformation of keratin (e.g., a compound that effectively alters the secondary and/or tertiary structure of keratin).

As used herein, the term "ester" refers to a compound of formula RC(=O)OR', wherein R is selected from the group consisting of hydrogen, a linear or branched alkyl, alkenyl, or alkynyl group, a carbocyclic group, or a heterocyclic group and R' is selected from the group consisting of a linear or branched alkyl, alkenyl, or alkynyl group, a carbocyclic group, or a heterocyclic group. Example esters include, but are not limited to, ethyl acetate, allyl hexanoate, benzyl acetate, butyl acetate, butyl butyrate, butyl propanoate, ethyl benzoate, ethyl butyrate, ethyl hexanoate, ethyl cinnamate, ethyl formate, ethyl heptanoate, isobutyl acetate, isobutyl formate, isoamyl acetate, and the like.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5 to 20 ring atoms, for example 5 to 20, 5 to 15, 5 to 10, 5 to 8, or 5 to 6 ring atoms, and 1, 2, 3 or 4 heteroatom ring members independently selected from nitrogen, sulfur and oxygen. Exemplary five-membered ring heteroaryls include, but are not limited to, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. Exemplary six-membered ring heteroaryls include, but are not limited to, pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. In some embodiments, the heterocycloalkyl has 5 to 20 ring atoms, for example 5 to 20, 5 to 15, 5 to 10, 5 to 8, or 5 to 6 ring atoms, and 1, 2, 3 or 4 heteroatom ring members independently selected from nitrogen, sulfur and oxygen. Heterocycloalkyl groups can also include spirocycles. Example heterocycloalkyl groups include, but are not limited to, pyrrolidin-2-on-yl, 1,3-isoxazolidin-2-on-yl, pyranyl, tetrahydropyranyl, oxetanyl, azetidinyl, morpholinyl, thiomorpholinyl, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)₂, etc.). The heterocycloalkyl group can be attached through a ring-forming carbon atom or a ring-forming heteroatom. In some embodiments, the heterocycloalkyl group contains 0 to 3 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, and the like. A heterocycloalkyl group containing a fused aromatic ring can be attached through any ring-forming atom including a ring-forming atom of the fused aromatic ring.

At certain places, the definitions or embodiments refer to specific rings (e.g., a furan ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "halide" refers to fluoride, chloride, bromide, or iodide.

As used herein, the term "guanidinium salt" refers to a compound of the following formula:

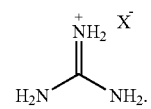

where X⁻ is an anion (e.g., halide, nitrate, acetate, and the like). Example guanidinium salts include, for example, guanidinium chloride, guanidinium bromide, guanidinium iodide, guanidinium hydroxide, guanidinium acetate, guanidinium thiocyanate, guanidinium nitrate, and the like.

As used herein, the term "base" refers to a base approved for cosmetic and/or pharmaceutical applications. Example bases include, but are not limited to, lithium hydroxide, sodium hydroxide, potassium hydroxide, magnesium hydroxide, calcium hydroxide, sodium carbonate, potassium carbonate, calcium carbonate, sodium bicarbonate, potassium bicarbonate, and the like.

As used herein, the term "reducing agent" refers to any reducing agent capable of reducing disulfide bonds in keratinized structures. Example reducing agents include, but are not limited to thiols (e.g., DTT (2,3 dihydroxybutane-1,4-dithiol) or its isomer DTE (2,3 dihydroxybutane-1,4-dithiol), mercaptoethanol, thioglycolate, cysteine), sulfites, bisulfites, sulfides, bisulfides or TCEP (tris(2-carboxyethyl) phosphine), or salt forms of any of the foregoing.

As used herein, the term "surfactant" refers to a compound that reduces surface tension between two liquid or between a liquid and a solid. Example anionic surfactants include, but are not limited to, sodium dodecyl sulfate, sodium dodecyl benzenesulfonate, sodium lauroyl sarcosinate, perfluorobutanesulfonic acid, perfluorononanoate, perfluorooctanoate, ammonium lauryl sulfate, sodium laureth sulfate, sodium myreth sulfate, and the like. Example cationic surfactants include, but are not limited to benzalkonium chloride, cetrimonium bromide, tetramethylammonium hydroxide, cetylpyridinium chloride, benzethonium chloride, dimethyldioctadecylammonium chloride, and dioctadecyldimethylammonium bromide, and the like. Example non-ionic surfactants include, but are not limited to, triton X-100, polysorbate 80, polysorbate 20, decyl glucoside, octaethylene glycol monododecyl ether, pentaethylene glycol monododecyl ether, lauryl glucoside, decyl glucoside, octyl glucoside, glyceryl laurate, lauryldimethylamine oxide, and the like.

Disentangling Composition

The present application provides, inter alia, a composition comprising:

(i) one or more independently selected reducing agents; and (ii) one or more independently selected disentangling agents.

In some embodiments, the one or more independently selected disentangling agents is selected from the group consisting of an alkanolamine, an amine, an amide, an alcohol, an amino acid, a surfactant, an anhydride, a guanidinium salt, an ester, and combinations thereof.

In some embodiments, each of the one or more independently selected reducing agents is a disulfide bond reducing agent. In some embodiments, each of the one or more independently selected reducing agents is selected from the group consisting of a thiol compound, a sulfite compound, a bisulfite compound, a sulfide compound, a bisulfide compound, and tris(2-carboxyethyl)phosphine (TCEP), or salt forms of any of the foregoing.

In some embodiments, at least one of the one or more independently selected reducing agents is a thiol. In some embodiments, at least one of the one or more independently selected reducing agents is selected from the group consisting of DTT (2,3 dihydroxybutane-1,4-dithiol), DTE (2,3 dihydroxybutane-1,4-dithiol), mercaptoethanol, thioglycolic acid and salts thereof (e.g., thioglycolate), thiolactic acid and salts thereof (e.g., thiolactate), sodium metabisulfite, dithiothreitol, and cysteine. In some embodiments, at least one of the one or more independently selected reducing agents is selected from the group consisting of DTT (2,3 dihydroxybutane-1,4-dithiol), DTE (2,3 dihydroxybutane-1,4-dithiol), mercaptoethanol, thioglycolate, and cysteine. In some embodiments, the reducing agent is cysteine.

In some embodiments, at least one of the one or more disentangling agents is an alkanolamine. In some embodiments, the alkanolamine comprises from about 1 to about 20 carbon atoms, for example, from 1 to 20 carbon atoms, from 1 to 15 carbon atoms, from 1 to 10 carbon atoms, 1 to 8 carbon atoms, or from 1 to 6 carbon atoms. In some embodiments, the alkanolamine comprises 1 hydroxyl group and 1 amine group. In some embodiments, the alkanolamine comprises two hydroxyl groups and 1 amine group. In some embodiments, the alkanolamine comprises two hydroxyl groups and 2 amine groups. In some embodiments, the alkanolamine is selected from the group consisting of ethanolamine, heptaminol, propanolamine, 2-(2-aminoethoxy)ethanol, and 2-amino-4-octadecene-1,3-diol. In some embodiments, the alkanolamine is 2-(2-aminoethoxy)ethanol.

In some embodiments, at least one of the one or more disentangling agents is an amine. In some embodiments, the amine comprises 1 to 20 carbon atoms, for example, from 1 to 20 carbon atoms, from 1 to 15 carbon atoms, from 1 to 10 carbon atoms, 1 to 8 carbon atoms, or from 1 to 6 carbon atoms. In some embodiments, the amine is selected from the group consisting of a mono($C_{1-20}$ alkyl)amine, di($C_{1-20}$ alkyl)amine, alkyl)amine, wherein each $C_{1-20}$ alkyl may be optionally substituted. In some embodiments, the amine is selected from the group consisting of a mono($C_{1-20}$ alkyl)amine, di($C_{1-20}$ alkyl)amine, alkyl)amine, wherein each $C_{1-20}$ alkyl may be optionally substituted. In some embodiments, the amine is selected from the group consisting of n-propylamine, isopropylamine, methylamine, dimethylamine, and trimethylamine.

In some embodiments, at least one of the one or more disentangling agents is an amide. In some embodiments, the amide comprises from about 1 to about 20 carbon atoms, for example, from 1 to 20 carbon atoms, from 1 to 15 carbon atoms, from 1 to 10 carbon atoms, 1 to 8 carbon atoms, or from 1 to 6 carbon atoms. In some embodiments, the amide is dimethylacetamide or carbamide. In some embodiments, the amide is dimethylacetamide.

In some embodiments, at least one of the one or more disentangling agents is an alcohol. In some embodiments, the alcohol is a monohydric alcohol or a polyhydric alcohol. In some embodiments, the alcohol is a monohydric alcohol comprising 1 to 20 carbon atoms, for example, from 1 to 20 carbon atoms, from 1 to 15 carbon atoms, from 1 to 10 carbon atoms, 1 to 8 carbon atoms, or from 1 to 6 carbon atoms. In some embodiments, the alcohol is a polyhydric alcohol comprising 1 to 20 carbon atoms, for example, from 1 to 20 carbon atoms, from 1 to 15 carbon atoms, from 1 to 10 carbon atoms, 1 to 8 carbon atoms, or from 1 to 6 carbon atoms. In some embodiments, the alcohol is a monohydric alcohol selected from the group consisting of ethanol, isopropanol, and n-butanol. In some embodiments, the alcohol is a polyhydric alcohol selected from the group consisting of ethylene glycol, propylene glycol, glycerol, erythritol, xylitol, mannitol, 1,2,3,4-butanetetrol, and volemitol. In some embodiments, the alcohol is a polyhydric alcohol selected from the group consisting of ethylene glycol, propylene glycol, glycerol, erythritol, xylitol, mannitol, and volemitol.

In some embodiments, at least one of the one or more disentangling agents is a surfactant. In some embodiments, the surfactant is an anionic surfactant. In some embodiments, the anionic surfactant is selected from the group consisting of sodium dodecyl sulfate, sodium dodecyl benzenesulfonate, sodium lauroyl sarcosinate, perfluorobutanesulfonic acid, and ammonium lauryl sulfate. In some embodiments, the surfactant is a cationic surfactant. In some embodiments, the cationic surfactant is selected from the group consisting of benzalkonium chloride, cetrimonium bromide, and tetramethylammonium hydroxide. In some embodiments, the surfactant is a non-ionic surfactant. In some embodiments, the non-ionic surfactant is selected from the group consisting of triton X-100, polysorbate 80, polysorbate 20, and decyl glucoside.

In some embodiments, at least one of the one or more disentangling agents is an anhydride. In some embodiments, the anhydride comprises from 2 to 20 carbon atoms, for example, from 2 to 20 carbon atoms, from 2 to 15 carbon atoms, from 2 to 10 carbon atoms, 2 to 8 carbon atoms, or from 2 to 6 carbon atoms. In some embodiments, the anhydride is selected from the group consisting of acetic anhydride, maleic anhydride, butyric anhydride, succinic anhydride, and methylsuccinic anhydride.

In some embodiments, at least one of the one or more disentangling agents is a guanidinium salt. In some embodiments, the guanidinium salt is guanidinium chloride.

In some embodiments, at least one of the one or more disentangling agents is an ester. In some embodiments, the ester comprises from 2 to 20 carbon atoms, for example, from 2 to 20 carbon atoms, from 2 to 15 carbon atoms, from 2 to 10 carbon atoms, 2 to 8 carbon atoms, or from 2 to 6 carbon atoms. In some embodiments, the ester is ethyl acetate.

In some embodiments, the composition comprises:
(i) a reducing agent; and
(ii) a disentangling agent;
wherein the disentangling agent is selected from the group consisting of an alkanolamine, an amine, an amide, an alcohol, an amino acid, a surfactant, an anhydride, a guanidinium salt, an ester, and combinations thereof.

In some embodiments, the composition comprises:
(i) a reducing agent; and
(ii) a disentangling agent;
wherein the reducing agent is selected from the group consisting of a thiol compound, a sulfite compound, a bisulfite compound, a sulfide compound, a bisulfide compound, and tris(2-carboxyethyl)phosphine (TCEP), or salt forms of any of the foregoing; and
the disentangling agent is selected from the group consisting of an alkanolamine, an amine, an amide, an alcohol, an amino acid, a surfactant, an anhydride, a guanidinium salt, an ester, and combinations thereof.

In some embodiments, the composition comprises:
(i) a reducing agent; and
(ii) a disentangling agent;
wherein the reducing agent is selected from the group consisting of 2,3 dihydroxybutane-1,4-dithiol (DTT), 2,3 dihydroxybutane-1,4-dithiol (DTE), mercaptoethanol, thioglycolate, cysteine, a sulfite compound, a bisulfite compound, a sulfide compound, a bisulfide compound, and tris(2-carboxyethyl)phosphine (TCEP), or salt forms of any of the foregoing; and and the disentangling agent is selected from the group consisting of an alkanolamine, an amine, an amide, an alcohol, an amino acid, a surfactant, an anhydride, a guanidinium salt, an ester, and combinations thereof.

In some embodiments, the composition comprises:
(i) a reducing agent; and
(ii) a disentangling agent;
wherein the reducing agent is cysteine and the disentangling agent is selected from the group consisting of an alkanolamine, an amine, an amide, an alcohol, an amino acid, a surfactant, an anhydride, a guanidinium salt, an ester, and combinations thereof.

In some embodiments, the composition comprises:
(i) a reducing agent; and
(ii) a disentangling agent;
wherein the reducing agent is cysteine and the disentangling agent is selected from the group consisting of 2-(2-aminoethoxy)ethanol, sodium dodecyl sulfate, dimethylacetamide, and ethyl acetate.

In some embodiments, the composition comprises:
(i) a reducing agent; and
(ii) a disentangling agent;
wherein the reducing agent is cysteine and the disentangling agent is 2-(2-aminoethoxy)ethanol.

In some embodiments, the composition comprises:
(i) a reducing agent; and
(ii) a disentangling agent;
wherein the reducing agent is cysteine and the disentangling agent is sodium dodecyl sulfate.

In some embodiments, the composition comprises:
(i) a reducing agent; and
(ii) a disentangling agent;
wherein the reducing agent is cysteine and the disentangling agent is dimethylacetamide.

In some embodiments, the composition comprises:
(i) a reducing agent; and
(ii) a disentangling agent;
wherein the reducing agent is cysteine and the disentangling agent is ethyl acetate.

In some embodiments, the total concentration of the one or more reducing agents is from about 0.05 to about 5 mol/L, for example, from about 0.05 to about 5, from about 0.05 to about 4, from about 0.05 to about 3, from about 0.05 to about 2, from about 0.05 to about 1, from about 0.05 to about 0.5, from about 0.05 to about 0.1, from about 0.1 to about 5, from about 0.1 to about 4, from about 0.1 to about 3, from about 0.1 to about 2, from about 0.1 to about 1, from about 0.1 to about 0.5, from about 0.5 to about 5, from about 0.5 to about 4, from about 0.5 to about 3, from about 0.5 to about 2, from about 0.5 to about 1, from about 1 to about 5, from about 1 to about 4, from about 1 to about 3, from about 1 to about 2, from about 2 to about 5, from about 2 to about 4, from about 2 to about 3, from about 3 to about 5, from about 3 to about 4, or from about 4 to about 5 mol/L. In some embodiments, the total concentration of the one or more independently selected reducing agents is from about 0.05 mol/L to about 2 mol/L. In some embodiments, the total concentration of the one or more independently selected reducing agents is from about 0.05 mol/L to about 1.5 mol/L. In some embodiments, the total concentration of the one or more independently selected reducing agents is from about 0.1 mol/L to about 1 mol/L.

In some embodiments, the total concentration of the one or more reducing agents is from about 0.1 to about 200 wt %, based on the weight of hair, for example, from about 0.1 to about 200 wt %, from about 0.1 to about 150 wt %, from about 0.1 to about 100 wt %, from about 0.1 to about 50 wt %, from about 0.1 to about 25 wt %, from about 0.1 to about 10 wt %, from about 0.1 to about 5 wt %, from about 0.1 to about 1 wt %, from about 0.1 to about 0.5 wt %, from about 0.5 to about 200 wt %, from about 0.5 to about 150 wt %, from about 0.5 to about 100 wt %, from about 0.5 to about 50 wt %, from about 0.5 to about 25 wt %, from about 0.5 to about 10 wt %, from about 0.5 to about 5 wt %, from about 0.5 to about 1 wt %, from about 1 to about 200 wt %, from about 1 to about 150 wt %, from about 1 to about 100 wt %, from about 1 to about 50 wt %, from about 1 to about 25 wt %, from about 1 to about 10 wt %, from about 1 to about 5 wt %, from about 5 to about 200 wt %, from about 5 to about 150 wt %, from about 5 to about 100 wt %, from about 5 to about 50 wt %, from about 5 to about 25 wt %, from about 5 to about 10 wt %, from about 10 to about 200 wt %, from about 10 to about 150 wt %, from about 10 to about 100 wt %, from about 10 to about 50 wt %, from about 10 to about 25 wt %, from about 25 to about 200 wt %, from about 25 to about 150 wt %, from about 25 to about 100 wt %, from about 25 to about 50 wt %, from about 50 to about 200 wt %, from about 50 to about 150 wt %, from about 50 to about 100 wt %, from about 100 to about 200 wt %, from about 100 to about 150 wt %, or from about 150 to about 200 wt % based on the weight of hair. In some embodiments, the total concentration of the one or more reducing agents is from about 5 to about 30 wt %, based on the weight of hair.

In some embodiments, the total concentration of the one or more disentangling agents is from about 0.01 mol/L to about 11 mol/L, for example from about 0.01 to about 11, from about from about 0.01 to about 10, from about 0.01 to about 8, from about 0.01 to about 6, from about 0.01 to about 4, from about 0.01 to about 2, from about 0.01 to about 1, from about 0.01 to about 0.5, from about 0.01 to about 0.1, from about 0.1 to about 11, from about from about 0.1 to about 10, from about 0.1 to about 8, from about 0.1 to about 6, from about 0.1 to about 4, from about 0.1 to about 2, from about 0.1 to about 1, from about 0.1 to about 0.5, from about 0.5 to about 11, from about from about 0.5 to about 10, from about 0.5 to about 8, from about 0.5 to about 6, from about 0.5 to about 4, from about 0.5 to about 2, from about 0.5 to about 1, from about 1 to about 11, from about from about 1 to about 10, from about 1 to about 8, from about 1 to about 6, from about 1 to about 4, from about 1 to about 2, from about 2 to about 11, from about from about 2 to about 10, from about 2 to about 8, from about 2 to about 6, from about 2 to about 4, from about 4 to about 11, from about from about 4 to about 10, from about 4 to about 8, from about 4 to about 6, from about 6 to about 11, from about from about 6 to about 10, from about 6 to about 8, from about 8 to about 11, from about from about 8 to about 10, or from about 10 to about 11 mol/L. In some embodiments, the total concentration of the one or more disentangling agents is from about 1 mol/L to about 10 mol/L. In some embodiments, the total concentration of the one or more disentangling agents is from about 1 mol/L to about 3 mol/L. In some embodiments, the total concentration of the one or more disentangling agents is from about 0.1 mol/L to about 10 mol/L. In some embodiments, the total concentration of the one or more disentangling agents is from about 0.01 mol/L to about 3 mol/L.

In some embodiments, the pH of the composition is from about 5 to about 13, for example from about 5 to about 13, from about 5 to about 12, from about 5 to about 11, from about 5 to about 10, from about 5 to about 9, from about 5 to about 8, from about 5 to about 7, from about 5 to about 6, from about 6 to about 13, from about 6 to about 12, from about 6 to about 11, from about 6 to about 10, from about 6 to about 9, from about 6 to about 8, from about 6 to about 7, from about 7 to about 13, from about 7 to about 12, from about 7 to about 11, from about 7 to about 10, from about 7 to about 9, from about 7 to about 8, from about 8 to about 13, from about 8 to about 12, from about 8 to about 11, from about 8 to about 10, from about 8 to about 9, from about 9 to about 13, from about 9 to about 12, from about 9 to about 11, from about 9 to about 10, from about 10 to about 13, from about 10 to about 12, from about 10 to about 11, from about 11 to about 13, from about 11 to about 12, or from about 12 to about 13. In some embodiments, the pH of the composition is from about 6 to about 11. In some embodiments, the pH of the composition is from about 6 to about 9.

In some embodiments, the composition further comprises a base. In some embodiments, the base is selected from the group consisting of lithium hydroxide, sodium hydroxide, and potassium hydroxide. In some embodiments, the base is sodium hydroxide.

In some embodiments, the composition is substantially free of aldehydes. In some embodiments, the composition comprises less than about 0.2% by weight aldehydes, for example, less than about 0.2%, less than about 0.15%, less than about 0.1%, less than about 0.05%, or less than about 0.01% by weight. In some embodiments, the composition is substantially free of formaldehyde. In some embodiments, the composition comprises less than about 0.2% by weight formaldehyde, for example, less than about 0.2%, less than about 0.15%, less than about 0.1%, less than about 0.05%, or less than about 0.01% by weight. In some embodiments, the composition comprises less than about 0.2% by weight formaldehyde. In some embodiments, the composition comprises less than about 0.1% by weight formaldehyde. In some embodiments, the composition comprises less than about 0.05% by weight formaldehyde.

Crosslinking Compositions

The present application further provides a composition, comprising:

(i) one or more independently selected polycarboxylic acids;

(ii) one or more independently selected alkali metal hypophosphites; and (iii) one or more independently selected crosslinking agents.

In some embodiments, each of the one or more independently selected crosslinking agents is selected from the group consisting of a carbohydrate, an amino acid, a peptide, an oligopeptide, a protein hydrolysate, an alkanolamine, an alcohol, and combinations thereof.

In some embodiments, at least one of the one or more independently selected polycarboxylic acids is selected from the group consisting of citric acid, oxalic acid, malonic acid, succinic acid, aconitic acid, adipic acid, pimelic acid, suberic acid, glutaric acid, azeliaic acid, and sebacic acid. In some embodiments, at least one of the one or more independently selected polycarboxylic acids is citric acid.

In some embodiments, at least one of the one or more independently selected alkali metal hypophosphites is selected from the group consisting of lithium hypophosphite, sodium hypophosphite, and potassium hypophosphite. In some embodiments, at least one of the one or more independently selected alkali metal hypophosphites is sodium hypophosphite.

In some embodiments, at least one of the one or more independently selected crosslinking agents is a carbohydrate. In some embodiments, at least one of the one or more independently selected carbohydrates is a monosaccharide. In some embodiments, at least one of the one or more independently selected monosaccharides is selected from the group consisting of glucose, fructose, and galactose. In some embodiments, at least one of the one or more independently selected carbohydrates is a disaccharide. In some embodiments, at least one of the one or more independently selected disaccharides is selected from the group consisting of sucrose, lactulose, maltose, and cellobiose. In some embodiments, at least one of the one or more independently selected carbohydrates is a polysaccharide. In some embodiments, at least one of the one or more independently selected polysaccharides is selected from the group consisting of starch, cellulose, and pectin.

In some embodiments, at least one of the one or more independently selected carbohydrates is an oxidized monosaccharide. In some embodiments, at least one of the one or more independently selected oxidized monosaccharides is prepared from a monosaccharide selected from the group consisting of glucose, fructose, galactose, glucosamine, dihydroxyacetone, erythrose, threose, erythrulose, arabinose, lyxose, ribose, xylose, ribulose, xylulose, allose, altrose, mannose, gulose, idose, talose, psicose, sorbose, tagatose, sedoheptulose, rhamnose, and mannoheptulose.

In some embodiments, at least one of the one or more independently selected carbohydrates is an oxidized disaccharide. In some embodiments, at least one of the one or more independently selected oxidized disaccharides is prepared from a disaccharide selected from the group consisting of sucrose, lactose, maltose, trehalose, lactulose, cellobiose, chitobiose, kojibiose, nigerose, isomaltose, sophorose, laminaribiose, gentiobiose, turanose, maltulose, palatinose, gentiobiulose, rutinulose, xylobiose, mannobiose, melibiose, melibiulose, and rutinose. In some embodiments, at least one of the oxidized disaccharides is oxidized sucrose.

In some embodiments, at least one of the one or more independently selected carbohydrates is an oxidized oligosaccharide. In some embodiments, at least one of the one or more independently selected oxidized oligosaccharides is prepared from an oligosaccharide selected from the group consisting of isomaltotriose, nigerotriose, maltotriose, melezitose, maltotriulose, kestose, lychnose, maltotetraose, nigerotetraose, nystose, sesamose, starchyose, raffinose, fructo-oligosaccharide, galactooligosaccharide, mannan oligosaccharide, *Brucella* M Tetrasaccharide, and thiooligosaccharide.

In some embodiments, at least one of the one or more independently selected carbohydrates is an oxidized polysaccharide. In some embodiments, at least one of the one or more independently selected oxidized polysaccharides is prepared from a polysaccharide selected from the group consisting of cellulose, amylose, amylopectin, glycogen, chitin, chitosan, alginate, callose, carrageenan, agar, fucoidan, laminarin, curdlan, xylan, chrysolaminarin, arabinoxylan, amylose, mannan, fucoidan, galactomannan, arabinoxylan, amylopectin, pectin, xanthan gum, welan gum, gellan gum, diutan gum, and pullulan.

In some embodiments, at least one of the one or more independently selected crosslinking agents is an amino acid. In some embodiments, at least one of the one or more independently selected amino acids is a synthetic amino acid. Example synthetic amino acids include, but are not limited to, (S)-(−)-1-[N-(1-ethoxycarbonyl-3-phenylpropyl)-N-trifluoroacetyl]-L-lysine, DL-5-hydroxylysine hydrochloride, (5R)-5-hydroxy-L-lysine dihydrochloride monohydrate, L-2-amino-3-guanidinopropionic acid hydrochloride, 4-guanidinobutyric acid, N-Benzoyl-(2R,3S)-3-phenylisoserine, cycloserine, isoserine, isoserine, 3-phenylserine hydrate, and thyroxine. In some embodiments, at least one of the one or more independently selected amino acids is a natural amino acid. In some embodiments, at least one of the one or more independently selected natural amino acids is selected from the group consisting of lysine, arginine, histidine, serine, and threonine. In some embodiments, at least one of the one or more independently selected natural amino acids is lysine.

In some embodiments, at least one of the one or more independently selected crosslinking agent is selected from the group consisting of a peptide, an oligopeptide, and a protein hydrolysate. Examples of peptides and oligopeptides that may be used as crosslinking agents may be found, for example in U.S. Pat. No. 8,952,095, the disclosure of which is incorporated by reference herein in its entirety.

In some embodiments, at least one of the one or more independently selected crosslinking agents is an alkanolamine. In some embodiments, at least one of the one or more independently selected alkanolamines comprises from about 1 to about 20 carbon atoms, for example, from 1 to 20 carbon atoms, from 1 to 15 carbon atoms, from 1 to 10 carbon atoms, 1 to 8 carbon atoms, or from 1 to 6 carbon atoms. In some embodiments, at least one of the one or more independently selected alkanolamines comprises 1 hydroxyl group and 1 amine group. In some embodiments, at least one of the one or more independently selected alkanolamines comprises 2 hydroxyl groups and 1 amine group. In some embodiments, at least one of the one or more independently selected alkanolamines comprises 2 hydroxyl groups and 2 amine groups. In some embodiments, at least one of the one or more independently selected alkanolamines is selected from the group consisting of ethanolamine, triethanolamine, heptaminol, propanolamine, 2-(2-aminoethoxy)ethanol, and 2-amino-4-octadecene-1,3-diol. In some embodiments, at least one of the one or more independently selected alkanolamines is 2-(2-aminoethoxy)ethanol.

In some embodiments, at least one of the one or more independently selected crosslinking agent is an alcohol. In some embodiments, at least one of the one or more independently selected alcohols is a polyhydric alcohol. In some embodiments, at least one of the one or more independently selected alcohols is a polyhydric alcohol comprising 1 to 20 carbon atoms, for example, from 1 to 20 carbon atoms, from 1 to 15 carbon atoms, from 1 to 10 carbon atoms, 1 to 8 carbon atoms, or from 1 to 6 carbon atoms. In some embodiments, at least one of the one or more independently selected polyhydric alcohols is selected from the group consisting of ethylene glycol, propylene glycol, glycerol, erythritol, xylitol, mannitol, 1,2,3,4-butanetetrol, and volemitol. In some embodiments, the alcohol is a polyhydric alcohol selected from the group consisting of ethylene glycol, propylene glycol, glycerol, erythritol, xylitol, mannitol, and volemitol. In some embodiments, at least one of the one or more independently selected polyhydric alcohols is glycerol or mannitol.

In some embodiments, the composition comprises from about 0.1 mol/L to about 1.5 mol/L of polycarboxylic acid, for example, from about 0.1 to about 1.5, from about 0.1 to about 1.2, from about 0.1 to about 1.0, from about 0.1 to about 0.8, from about 0.1 to about 0.6, from about 0.1 to about 0.4, from about 0.1 to about 0.2, from about 0.2 to about 1.5, from about 0.2 to about 1.2, from about 0.2 to about 1.0, from about 0.2 to about 0.8, from about 0.2 to about 0.6, from about 0.2 to about 0.4, from about 0.4 to about 1.5, from about 0.4 to about 1.2, from about 0.4 to about 1.0, from about 0.4 to about 0.8, from about 0.4 to about 0.6, from about 0.6 to about 1.5, from about 0.6 to about 1.2, from about 0.6 to about 1.0, from about 0.6 to about 0.8, from about 0.8 to about 1.5, from about 0.8 to about 1.2, from about 0.8 to about 1.0, from about 1.0 to about 1.5, from about 1.0 to about 1.2, or from about 1.2 to about 1.5 mol/L. In some embodiments, the composition comprises about from about 0.1 mol/L to about 1.5 mol/L of polycarboxylic acid. In some embodiments, the composition comprises about from about 0.75 mol/L to about 1.2 mol/L of polycarboxylic acid.

In some embodiments, composition comprises from about 0.5 mol/L to about 1.5 mol/L of alkali metal hypophosphite, for example, from about 0.5 to about 1.5, from about 0.5 to about 1.2, from about 0.5 to about 1.0, from about 0.5 to about 0.75, from about 0.5 to about 0.6, from about 0.6 to about 1.5, from about 0.6 to about 1.2, from about 0.6 to about 1.0, from about 0.6 to about 0.75, from about 0.75 to about 1.5, from about 0.75 to about 1.2, from about 0.75 to about 1.0, from about 1.0 to about 1.5, from about 1.0 to about 1.2, or from about 1.2 to about 1.5 mol/L. In some embodiments, the composition comprises from about 0.5 mol/L to about 1.5 mol/L of the alkali metal hypophosphite. In some embodiments, the composition comprises from about 0.75 mol/L to about 1.2 mol/L of alkali metal hypophosphite.

In some embodiments, the composition comprises from about 0.01 mol/L to about 15 mol/L of the crosslinking agent, for example, from about 0.01 to about 15, from about from about 0.01 to about 10, from about 0.01 to about 8, from about 0.01 to about 6, from about 0.01 to about 4, from about 0.01 to about 3, from about 0.01 to about 1, from about 0.01 to about 0.5, from about 0.01 to about 0.1, from about 0.05 to about 15, from about from about 0.05 to about 10, from about 0.05 to about 8, from about 0.05 to about 6, from about 0.05 to about 4, from about 0.05 to about 3, from about 0.05 to about 1, from about 0.05 to about 0.5, from about 0.05 to about 0.1, from about 0.1 to about 15, from about 0.1 to about 10, from about 0.1 to about 8, from about 0.1 to about 6, from about 0.1 to about 4, from about 0.1 to about 3, from about 0.1 to about 1, from about 0.1 to about 0.5, from about 0.5 to about 15, from about 0.5 to about 10, from about 0.5 to about 8, from about 0.5 to about 6, from about 0.5 to about 4, from about 0.5 to about 3, from about 0.5 to about 1, from about 1 to about 15, from about 1 to about 10, from about 1 to about 8, from about 1 to about 6, from about 1 to about 4, from about 1 to about 3, from about 2 to about 15, from about 2 to about 10, from about 2 to about 8, from about 2 to about 6, from about 2 to about 4, from about 4 to about 15, from about 4 to about 10, from about 4 to about 8, from about 4 to about 6, from about 6 to about 15, from about 6 to about 10, from about 6 to about 8, from about 8 to about 15, from about 8 to about 10, or from about 10 to about 15 mol/L. In some embodiments, the composition comprises from about 0.01 mol/L to about 10 mol/L of the crosslinking agent. In some embodiments, the composition comprises from about 0.1 mol/L to about 10 mol/L of the crosslinking agent. In some embodiments, the composition comprises from about 0.1 mol/L to about 3 mol/L of the crosslinking agent. In some embodiments, the composition comprises from about 0.5 mol/L to about 3 mol/L of the crosslinking agent. In some embodiments, the composition comprises from about 0.5 mol/L to about 1.2 mol/L of the crosslinking agent. In some embodiments, the composition comprises from about 0.5 mol/L to about 1.1 mol/L of the crosslinking agent.

In some embodiments, the total concentration of the one or more crosslinking agents is from about 0.1 to about 200 wt %, based on the weight of hair, for example, from about 0.1 to about 200 wt %, from about 0.1 to about 150 wt %, from about 0.1 to about 100 wt %, from about 0.1 to about 50 wt %, from about 0.1 to about 25 wt %, from about 0.1 to about 10 wt %, from about 0.1 to about 5 wt %, from about 0.1 to about 1 wt %, from about 0.1 to about 0.5 wt %, from about 0.5 to about 200 wt %, from about 0.5 to about 150 wt %, from about 0.5 to about 100 wt %, from about 0.5 to about 50 wt %, from about 0.5 to about 25 wt %, from about 0.5 to about 10 wt %, from about 0.5 to about 5 wt %, from about 0.5 to about 1 wt %, from about 1 to about 200 wt %, from about 1 to about 150 wt %, from about 1 to about 100 wt %, from about 1 to about 50 wt %, from about 1 to about 25 wt %, from about 1 to about 10 wt %, from about 1 to about 5 wt %, from about 5 to about 200 wt %, from about 5 to about 150 wt %, from about 5 to about 100 wt %, from about 5 to about 50 wt %, from about 5 to about 25 wt %, from about 5 to about 10 wt %, from about 10 to about 200 wt %, from about 10 to about 150 wt %, from about 10 to about 100 wt %, from about 10 to about 50 wt %, from about 10 to about 25 wt %, from about 25 to about 200 wt %, from about 25 to about 150 wt %, from about 25 to about 100 wt %, from about 25 to about 50 wt %, from about 50 to about 200 wt %, from about 50 to about 150 wt %, from about 50 to about 100 wt %, from about 100 to about 200 wt %, from about 100 to about 150 wt %, or from about 150 to about 200 wt % based on the weight of hair. In some embodiments, the total concentration of the one or more crosslinking agents is from about 5 to about 30 wt %, based on the weight of hair.

In some embodiments, the composition comprises:
(i) one or more independently selected polycarboxylic acids;
(ii) one or more independently selected alkali metal hypophosphites; and
(iii) one or more independently selected crosslinking agents;
wherein at least one of the one or more independently selected polycarboxylic acids is selected from the group consisting of citric acid, oxalic acid, malonic acid, succinic acid, aconitic acid, adipic acid, pimelic acid, suberic acid, glutaric acid, azeliaic acid, and sebacic acid;
at least one of the one or more independently selected alkali metal hypophosphites is selected from the group consisting of lithium hypophosphite, sodium hypophosphite, and potassium hypophosphite; and
at least one of the one or more independently selected crosslinking agents is selected from the group consisting of a carbohydrate, an amino acid, a peptide, an oligopeptide, a protein hydrolysate, an alkanolamine, and an alcohol.

In some embodiments, the composition comprises:
(i) one or more independently selected polycarboxylic acids;
(ii) one or more independently selected alkali metal hypophosphites; and
(iii) one or more independently selected crosslinking agents;
wherein at least one of the one or more independently selected polycarboxylic acids is citric acid;
at least one of the one or more independently selected alkali metal hypophosphites is selected from the group consisting of lithium hypophosphite, sodium hypophosphite, and potassium hypophosphite; and
at least one of the one or more independently selected crosslinking agents is selected from the group consisting of a carbohydrate, an amino acid, a peptide, an oligopeptide, a protein hydrolysate, an alkanolamine, and an alcohol.

In some embodiments, the composition comprises:
(i) one or more independently selected polycarboxylic acids;
(ii) one or more independently selected alkali metal hypophosphites; and
(iii) one or more independently selected crosslinking agents;
wherein at least one of the one or more independently selected polycarboxylic acids is citric acid;
at least one of the one or more independently selected alkali metal hypophosphites is sodium hypophosphite; and
at least one of the one or more independently selected crosslinking agents is selected from the group consisting of a carbohydrate, an amino acid, a peptide, an oligopeptide, a protein hydrolysate, an alkanolamine, and an alcohol.

In some embodiments, the composition comprises:
(i) a polycarboxylic acid;
(ii) an alkali metal hypophosphite; and
(iii) a crosslinking agent;
wherein the polycarboxylic acid is selected from the group consisting of citric acid, oxalic acid, malonic acid, succinic acid, aconitic acid, adipic acid, pimelic acid, suberic acid, glutaric acid, azeliaic acid, and sebacic acid;
the alkali metal hypophosphite is selected from the group consisting of lithium hypophosphite, sodium hypophosphite, and potassium hypophosphite; and
the crosslinking agent is selected from the group consisting of a carbohydrate, an amino acid, a peptide, an oligopeptide, a protein hydrolysate, an alkanolamine, and an alcohol.

In some embodiments, the composition comprises:
(i) a polycarboxylic acid;
(ii) an alkali metal hypophosphite; and
(iii) a crosslinking agent;
wherein the polycarboxylic acid is citric acid;
the alkali metal hypophosphite is selected from the group consisting of lithium hypophosphite, sodium hypophosphite, and potassium hypophosphite; and
the crosslinking agent is selected from the group consisting of a carbohydrate, an amino acid, a peptide, an oligopeptide, a protein hydrolysate, an alkanolamine, and an alcohol.

In some embodiments, the composition comprises:
(i) a polycarboxylic acid;
(ii) an alkali metal hypophosphite; and
(iii) a crosslinking agent;
wherein the polycarboxylic acid is citric acid;
the alkali metal hypophosphite is sodium hypophosphite; and
the crosslinking agent is selected from the group consisting of a carbohydrate, an amino acid, a peptide, an oligopeptide, a protein hydrolysate, an alkanolamine, and an alcohol.

In some embodiments, the composition comprises:
(i) from about 0.75 mol/L to about 1.2 mol/L polycarboxylic acid;
(ii) from about 0.75 mol/L to about 1.2 mol/L alkali metal hypophosphite; and
(iii) from about 0.5 mol/L to about 1.1 mol/L crosslinking agent;
wherein the polycarboxylic acid is selected from the group consisting of citric acid, oxalic acid, malonic acid, succinic acid, aconitic acid, adipic acid, pimelic acid, suberic acid, glutaric acid, azeliaic acid, and sebacic acid;
the alkali metal hypophosphite is selected from the group consisting of lithium hypophosphite, sodium hypophosphite, and potassium hypophosphite; and
the crosslinking agent is selected from the group consisting of a carbohydrate, an amino acid, a peptide, an oligopeptide, a protein hydrolysate, an alkanolamine, and an alcohol.

In some embodiments, the composition comprises:
(i) from about 0.75 mol/L to about 1.2 mol/L citric acid;
(ii) from about 0.75 mol/L to about 1.2 mol/L alkali metal hypophosphite; and
(iii) from about 0.5 mol/L to about 1.1 mol/L crosslinking agent;
wherein the alkali metal hypophosphite is selected from the group consisting of lithium hypophosphite, sodium hypophosphite, and potassium hypophosphite; and the crosslinking agent is selected from the group consisting of a carbohydrate, an amino acid, a peptide, an oligopeptide, a protein hydrolysate, an alkanolamine, and an alcohol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L of a crosslinking agent;
wherein the crosslinking agent is selected from the group consisting of a carbohydrate, an amino acid, a peptide, an oligopeptide, a protein hydrolysate, an alkanolamine, and an alcohol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L of a crosslinking agent;
wherein the crosslinking agent is selected from the group consisting of 2-(2-aminoethoxy)ethanol, lysine, glycerol, and mannitol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L of a crosslinking agent;
wherein the crosslinking agent is 2-(2-aminoethoxy)ethanol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L of a crosslinking agent;
wherein the crosslinking agent is lysine.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L of a crosslinking agent;
wherein the crosslinking agent is glycerol.

In some embodiments, the composition comprises:
(i) from about 0.75 mol/L to about 1.2 mol/L citric acid;
(ii) from about 0.75 mol/L to about 1.2 mol/L sodium hypophosphite; and
(iii) from about 0.5 mol/L to about 1.1 mol/L of a crosslinking agent;
wherein the crosslinking agent is mannitol.

The present application further provides a composition comprising one or more independently selected polycarboxylic acids provided herein. In some embodiments, the composition further comprises one or more independently selected alkali metal hypophosphites provided herein.

The present application further provides a second crosslinking composition comprising one or more independently selected crosslinking agents provided herein (e.g., a crosslinking composition comprising one or more independently selected oxidized saccharides provided herein). In some embodiments, the second crosslinking composition comprises one or more crosslinking agents wherein at least one of the crosslinking agents is oxidized sucrose. In some embodiments, the second crosslinking consists essentially of one or more independently selected crosslinking agents provided herein (e.g., the second crosslinking composition consists essentially of one or more independently selected oxidized saccharides provided herein). In some embodiments, the second crosslinking composition consists essentially of one or more crosslinking agents wherein at least one of the crosslinking agents is oxidized sucrose. In some embodiments, the second crosslinking composition consists essentially of one crosslinking agent provided herein (e.g., the second crosslinking composition consists essentially of one oxidized saccharide provided herein). In some embodiments, the second crosslinking composition consists essentially of one crosslinking agent which is oxidized sucrose.

In some embodiments, the second crosslinking composition comprises from about 0.001 mol/L to about 15 mol/L of the crosslinking agent, for example, for example, from about 0.001 to about 15, from about from about 0.001 to about 10, from about 0.001 to about 8, from about 0.001 to about 6, from about 0.001 to about 4, from about 0.001 to about 3, from about 0.001 to about 1, from about 0.001 to about 0.5, from about 0.001 to about 0.1, from about 0.001 to about 0.01, from about 0.01 to about 15, from about from about 0.01 to about 10, from about 0.01 to about 8, from about 0.01 to about 6, from about 0.01 to about 4, from about 0.01 to about 3, from about 0.01 to about 1, from about 0.01 to about 0.5, from about 0.01 to about 0.1, from about 0.05 to about 15, from about from about 0.05 to about 10, from about 0.05 to about 8, from about 0.05 to about 6, from about 0.05 to about 4, from about 0.05 to about 3, from about 0.05 to about 1, from about 0.05 to about 0.5, from about 0.05 to about 0.1, from about 0.1 to about 15, from about 0.1 to about 10, from about 0.1 to about 8, from about 0.1 to about 6, from about 0.1 to about 4, from about 0.1 to about 3, from about 0.1 to about 1, from about 0.1 to about 0.5, from about 0.5 to about 15, from about 0.5 to about 10, from about 0.5 to about 8, from about 0.5 to about 6, from about 0.5 to about 4, from about 0.5 to about 3, from about 0.5 to about 1, from about 1 to about 15, from about 1 to about 10, from about 1 to about 8, from about 1 to about 6, from about 1 to about 4, from about 1 to about 3, from about 2 to about 15, from about 2 to about 10, from about 2 to about 8, from about 2 to about 6, from about 2 to about 4, from about 4 to about 15, from about 4 to about 10, from about 4 to about 8, from about 4 to about 6, from about 6 to about 15, from about 6 to about 10, from about 6 to about 8, from about 8 to about 15, from about 8 to about 10, or from about 10 to about 15 mol/L. In some embodiments, the composition comprises from about 0.01 mol/L to about 10 mol/L of the crosslinking agent. In some embodiments, the composition comprises from about 0.1 mol/L to about 10 mol/L of the crosslinking agent. In some embodiments, the composition comprises from about 0.1 mol/L to about 3 mol/L of the crosslinking agent. In some embodiments, the composition comprises from about 0.5 mol/L to about 3 mol/L of the crosslinking agent. In some embodiments, the composition comprises from about 0.5 mol/L to about 1.2 mol/L of the crosslinking agent. In some embodiments, the composition comprises from about 0.5 mol/L to about 1.1 mol/L of the crosslinking agent. In some embodiments, the composition comprises from about 0.001 mol/L to about 0.01 mol/L.

In some embodiments, the total concentration of the one or more crosslinking agents is from about 0.1 to about 200 wt %, based on the weight of hair, for example, from about 0.1 to about 200 wt %, from about 0.1 to about 150 wt %, from about 0.1 to about 100 wt %, from about 0.1 to about 50 wt %, from about 0.1 to about 25 wt %, from about 0.1 to about 10 wt %, from about 0.1 to about 5 wt %, from about 0.1 to about 1 wt %, from about 0.1 to about 0.5 wt %, from about 0.5 to about 200 wt %, from about 0.5 to about 150 wt %, from about 0.5 to about 100 wt %, from about 0.5 to about 50 wt %, from about 0.5 to about 25 wt %, from about 0.5 to about 10 wt %, from about 0.5 to about 5 wt %, from about 0.5 to about 1 wt %, from about 1 to about 200 wt %, from about 1 to about 150 wt %, from about 1 to about 100 wt %, from about 1 to about 50 wt %, from about 1 to about 25 wt %, from about 1 to about 10 wt %, from about 1 to about 5 wt %, from about 5 to about 200 wt %, from about 5 to about 150 wt %, from about 5 to about 100 wt %, from about 5 to about 50 wt %, from about 5 to about 25 wt %, from about 5 to about 10 wt %, from about 10 to about 200 wt %, from about 10 to about 150 wt %, from about 10 to about 100 wt %, from about 10 to about 50 wt %, from about 10 to about 25 wt %, from about 25 to about 200 wt %, from about 25 to about 150 wt %, from about 25 to about 100 wt %, from about 25 to about 50 wt %, from about 50 to about 200 wt %, from about 50 to about 150 wt %, from about 50 to about 100 wt %, from about 100 to about 200 wt %, from about 100 to about 150 wt %, or from about 150 to about 200 wt % based on the weight of hair. In some embodiments, the total concentration of the one or more crosslinking agents is from about 5 to about 30 wt %, based on the weight of hair.

The present application further provides a third crosslinking composition comprising one or more independently selected crosslinking agents provided herein. In some embodiments, the third crosslinking composition further comprises one or more independently selected alkali metal hypophosphites provided herein or one or more independently selected polycarboxylic acids provided herein.

In some embodiments, the composition further comprises a solvent. In some embodiments, the solvent comprises an alcohol. In some embodiments, the solvent is selected from the group consisting of methanol, ethanol, and isopropanol. In some embodiments, the solvent comprises water.

In some embodiments, the pH of the composition is from about 3 to about 12, for example from about 1 to about 12, from about 1 to about 11, from about 1 to about 10, from about 1 to about 9, from about 1 to about 8, from about 1 to about 7, from about 1 to about 6, from about 2 to about 5, from about 1 to about 4, from about 1 to about 3, from about 3 to about 12, from about 3 to about 11, from about 3 to about 10, from about 3 to about 9, from about 3 to about 8, from about 3 to about 7, from about 3 to about 6, from about 2 to about 5, from about 3 to about 4, from about 4 to about 12, for example from about 4 to about 12, from about 4 to about 11, from about 4 to about 10, from about 4 to about 9, from about 4 to about 8, from about 4 to about 7, from about 4 to about 6, from about 2 to about 5, from about 5 to about 12, from about 5 to about 11, from about 5 to about 10, from about 5 to about 9, from about 5 to about 8, from about 5 to about 7, from about 5 to about 6, from about 6 to about 12, from about 6 to about 11, from about 6 to about 10, from about 6 to about 9, from about 6 to about 8, from about 6 to about 7, from about 7 to about 12, from about 7 to about 11, from about 7 to about 10, from about 7 to about 9, from about 7 to about 8, from about 8 to about 12, from about 8 to about 11, from about 8 to about 10, from about 8 to about 9, from about 9 to about 12, from about 9 to about 11, from about 9 to about 10, from about 10 to about 12, from about 10 to about 11, or from about 11 to about 12. In some embodiments, the pH of the composition is from about 5 to about 9. In some embodiments, the pH of the composition is from about 1 to about 5.5.

In some embodiments, the composition is substantially free of aldehydes. In some embodiments, the composition comprises less than about 2% by weight aldehydes, for example, less than about 2%, less than about 1.5%, less than about 1%, less than about 0.5%, or less than about 0.1% by weight. In some embodiments, the composition is substantially free of formaldehyde. In some embodiments, the composition comprises less than about 2% by weight formaldehyde, for example, less than about 2%, less than about 1.5%, less than about 1%, less than about 0.5%, or less than about 0.1% by weight. In some embodiments, the composition comprises less than about 2% by weight formaldehyde. In some embodiments, the composition comprises less than about 1% by weight formaldehyde. In some embodiments, the composition comprises less than about 0.5% by weight formaldehyde.

Methods of Use

The present application further provides a method of styling hair, the method comprising disassembling secondary structures of at least a portion of the hair. In some embodiments, the method comprises contacting the hair with a disentangling composition as provided herein, wherein the disentangling composition disassembles the secondary and tertiary structures of at least a portion of the hair.

The present application further provides a method of styling hair, the method comprising chemically crosslinking the hair. In some embodiments, the method comprises contacting the hair with a crosslinking composition provided herein, wherein the crosslinking composition chemically crosslinks at least a portion of the hair.

The present application further provides a method of styling hair, the method comprising:
(i) disassembling secondary structures of at least a portion of the hair; and
(ii) chemically crosslinking the hair.

In some embodiments, the method of styling hair comprises:
(i) contacting the hair with a disentangling composition provided herein, wherein the disentangling composition disassembles the secondary and tertiary structures of at least a portion of the hair; and
(ii) contacting the hair with a crosslinking composition provided herein, wherein the crosslinking composition chemically crosslinks at least a portion of the hair.

The present application further provides a method of styling hair, the method comprising:
(i) contacting the hair with a disentangling composition provided herein;
(ii) optionally heating the hair; and
(iii) shaping the hair to a specific style.

In some embodiments, the optional heating of step (ii) is performed at from about 20° C. to about 120° C., for example from about 20 to about 120, from about 20 to about 100, from about 20 to about 90, from about 20 to about 80, from about 20 to about 70, from about 20 to about 60, from about 20 to about 50, from about 20 to about 40, from about 20 to about 30, from about 30 to about 120, from about 30 to about 100, from about 30 to about 90, from about 30 to about 80, from about 30 to about 70, from about 30 to about 60, from about 30 to about 50, from about 30 to about 40, from about 40 to about 120, from about 40 to about 100, from about 40 to about 90, from about 40 to about 80, from about 40 to about 70, from about 40 to about 60, from about 40 to about 50, from about 50 to about 120, from about 50 to about 100, from about 50 to about 90, from about 50 to about 80, from about 50 to about 70, from about 50 to about 60, from about 60 to about 120, from about 60 to about 100, from about 60 to about 90, from about 60 to about 80, from about 60 to about 70, from about 70 to about 120, from about 70 to about 100, from about 70 to about 90, from about 70 to about 80, from about 80 to about 120, from about 80 to about 100, from about 80 to about 90, from about 90 to about 120, from about 90 to about 100, or from about 100 to about 120° C. In some embodiments, the optional heating of step (ii) is performed at from about 20° C. to about 90° C. In some embodiments, the optional heating of step (ii) is performed at from about 20° C. to about 80° C. In some embodiments, the optional heating of step (ii) is performed at from about 45° C. to about 55° C.

In some embodiments, the shaping of step (iii) is performed using a styling tool. In some embodiments, the styling tool is selected from the group consisting of a heating tool, a shaping tool, and a heating and shaping tool. In some embodiments, the styling tool is a flat iron or a curling iron.

In some embodiments, the method further comprises rinsing and drying the hair.

In some embodiments, the rinsing and drying is performed after waiting a sufficient time after the shaping of step (iii). In some embodiments, the sufficient time is from about 1 to about 90 minutes, for example, from about 1 to about 90, from about 1 to about 80, from about 1 to about 70, from about 1 to about 60, from about 1 to about 50, from about 1 to about 40, from about 1 to about 30, from about 1 to about 20, from about 1 to about 10, from about 1 to about 5, from about 1 to about 3, from about 3 to about 90, from about 3 to about 80, from about 3 to about 70, from about 3 to about 60, from about 3 to about 50, from about 3 to about 40, from about 3 to about 30, from about 3 to about 20, from about 3 to about 10, from about 3 to about 5, from about 5 to about 90, from about 5 to about 80, from about 5 to about 70, from about 5 to about 60, from about 5 to about 50, from about 5 to about 40, from about 5 to about 30, from about 5 to about 20, from about 5 to about 10, from about 10 to about 90, from about 10 to about 80, from about 10 to about 70, from about 10 to about 60, from about 10 to about 50, from about 10 to about 40, from about 10 to about 30, from about 10 to about 20, from about 20 to about 90, from about 20 to about 80, from about 20 to about 70, from about 20 to about 60, from about 20 to about 50, from about 20 to about 40, from about 20 to about 30, from about 30 to about 90, from about 30 to about 80, from about 30 to about 70, from about 30 to about 60, from about 30 to about 50, from about 30 to about 40, from about 40 to about 90, from about 40 to about 80, from about 40 to about 70, from about 40 to about 60, from about 40 to about 50, from about 50 to about 90, from about 50 to about 80, from about 50 to about 70, from about 50 to about 60, from about 60 to about 90, from about 60 to about 80, from about 60 to about 70, from about 70 to about 90, from about 70 to about 80, or from about 80 to about 90 minutes. In some embodiments, the sufficient time is from about 20 to about 45 minutes. In some embodiments, the sufficient time is from about 20 to 35 minutes.

In some embodiments, the drying is performed at from about 20 to about 90° C., for example, from about 20 to about 90° C., from about 20 to about 80° C., from about 20 to about 70° C., from about 20 to about 60° C., from about 20 to about 50° C., from about 20 to about 40° C., from about 20 to about 30° C., from about 30 to about 90° C., from about 30 to about 80° C., from about 30 to about 70° C., from about 30 to about 60° C., from about 30 to about 50° C., from about 30 to about 40° C., from about 40 to about 90° C., from about 40 to about 80° C., from about 40 to about 70° C., from about 40 to about 60° C., from about 40 to about 50° C., from about 50 to about 90° C., from about 50 to about 80° C., from about 50 to about 70° C., from about 50 to about 60° C., from about 60 to about 90° C., from about 60 to about 80° C., from about 60 to about 70° C., from about 70 to about 90° C., from about 70 to about 80° C., or from about 80 to about 90° C. In some embodiments, the drying is performed at from about 50° C. to about 80° C. In some embodiments, the method of styling hair comprises straightening the hair or curling the hair. In some embodiments, the method of styling hair comprises straightening the hair. In some embodiments, the method of styling hair comprises curling the hair.

In some embodiments, the method of styling hair comprises:
(i) contacting the hair with a disentangling composition provided herein;
(ii) optionally heating the hair;
(iii) shaping the hair to a specific style; and
(iv) rinsing and drying the hair.

In some embodiments, the method of styling hair comprises:
(i) contacting the hair with a disentangling composition provided herein;
(ii) heating the hair;
(iii) shaping the hair to a specific style; and
(iv) rinsing and drying the hair.

The present application further provides a method of styling hair, the method comprising contacting the hair with a crosslinking composition provided herein. In some embodiments, the method further comprises styling the hair prior to contacting the hair with a crosslinking composition provided herein.

In some embodiments, the method further comprises waiting a time sufficient to allow crosslinking. In some embodiments, the waiting is from about 1 minute to about 90 minutes, for example, from about 1 to about 90, from about 1 to about 80, from about 1 to about 70, from about 1 to about 60, from about 1 to about 50, from about 1 to about 40, from about 1 to about 30, from about 1 to about 20, from about 1 to about 10, from about 1 to about 5, from about 1 to about 3, from about 3 to about 90, from about 3 to about 80, from about 3 to about 70, from about 3 to about 60, from about 3 to about 50, from about 3 to about 40, from about 3 to about 30, from about 3 to about 20, from about 3 to about 10, from about 3 to about 5, from about 5 to about 90, from about 5 to about 80, from about 5 to about 70, from about 5 to about 60, from about 5 to about 50, from about 5 to about 40, from about 5 to about 30, from about 5 to about 20, from about 5 to about 10, from about 10 to about 90, from about 10 to about 80, from about 10 to about 70, from about 10 to about 60, from about 10 to about 50, from about 10 to about 40, from about 10 to about 30, from about 10 to about 20, from about 20 to about 90, from about 20 to about 80, from about 20 to about 70, from about 20 to about 60, from about 20 to about 50, from about 20 to about 40, from about 20 to about 30, from about 30 to about 90, from about 30 to about 80, from about 30 to about 70, from about 30 to about 60, from about 30 to about 50, from about 30 to about 40, from about 40 to about 90, from about 40 to about 80, from about 40 to about 70, from about 40 to about 60, from about 40 to about 50, from about 50 to about 90, from about 50 to about 80, from about 50 to about 70, from about 50 to about 60, from about 60 to about 90, from about 60 to about 80, from about 60 to about 70, from about 70 to about 90, from about 70 to about 80, or from about 80 to about 90 minutes. In some embodiments, the waiting is from about 1 minute to about 15 minutes. In some embodiments, the waiting is from about 1 minute to about 5 minutes.

In some embodiments, the method further comprises heating the hair. In some embodiments, the heating is performed at from about 20° C. to about 250° C., for example, from about 20 to about 250, from about 20 to about 230, from about 20 to about 210, from about 20 to about 190, from about 20 to about 170, from about 20 to about 150, from about 20 to about 130, from about 20 to about 110, from about 20 to about 90, from about 20 to about 70, from about 20 to about 50, from about 20 to about 30, from about 30 to about 250, from about 30 to about 230, from about 30 to about 210, from about 30 to about 190, from about 30 to about 170, from about 30 to about 150, from about 30 to about 130, from about 30 to about 110, from about 30 to about 90, from about 30 to about 70, from about 30 to about 50, from about 50 to about 250, from about 50 to about 230, from about 50 to about 210, from about 50 to about 190, from about 50 to about 170, from about 50 to about 150, from about 50 to about 130, from about 50 to about 110, from about 50 to about 90, from about 50 to about 70, from about 70 to about 250, from about 70 to about 230, from about 70 to about 210, from about 70 to about 190, from about 70 to about 170, from about 70 to about 150, from about 70 to about 130, from about 70 to about 110, from about 70 to about 90, from about 90 to about 250, from about 90 to about 230, from about 90 to about 210, from about 90 to about 190, from about 90 to about 170, from about 90 to about 150, from about 90 to about 130, from about 90 to about 110, from about 110 to about 250, from about 110 to about 230, from about 110 to about 210, from about 110 to about 190, from about 110 to about 170, from about 110 to about 150, from about 110 to about 130, from about 130 to about 250, from about 130 to about 230, from about 130 to about 210, from about 130 to about 190, from about 130 to about 170, from about 130 to about 150, from about 150 to about 250, from about 150 to about 230, from about 150 to about 210, from about 150 to about 190, from about 150 to about 170, from about 170 to about 250, from about 170 to about 230, from about 170 to about 210, from about 170 to about 190, from about 190 to about 250, from about 190 to about 230, from about 190 to about 210, from about 210 to about 250, from about 210 to about 230, or from about 230 to about 250° C. In some embodiments, the heating is performed at from about 100° C. to about 200° C. In some embodiments, the heating is performed at from about 150° C. to about 200° C. In some embodiments, the heating is performed at from about 50° C. to about 180° C. In some embodiments, the heating is performed at about 180° C.

In some embodiments, the method further comprises rinsing and drying the hair. In some embodiments, the rinsing and drying is performed at from about 30 minutes to about 48 hours after the contacting, for example, for example, at from about 30 minutes to about 48 hours, from about 30 minutes to about 36 hours, from about 30 minutes to about 24 hours, from about 30 minutes to about 18 hours, from about 30 minutes to about 12 hours, from about 30 minutes to about 8 hours, from about 30 minutes to about 6 hours, from about 30 minutes to about 4 hours, from about 30 minutes to about 2 hours, from about 30 minutes to about 1 hour, from about 1 hour to about 48 hours, from about 1 hour to about 36 hours, from about 1 hour to about 24 hours, from about 1 hour to about 18 hours, from about 1 hour to about 12 hours, from about 1 hour to about 8 hours, from about 1 hour to about 6 hours, from about 1 hour to about 4 hours, from about 1 hour to about 2 hours, from about 2 hours to about 48 hours, from about 2 hours to about 36 hours, from about 2 hours to about 24 hours, from about 2 hours to about 18 hours, from about 2 hours to about 12 hours, from about 2 hours to about 8 hours, from about 2 hours to about 6 hours, from about 2 hours to about 4 hours, from about 4 hours to about 48 hours, from about 4 hours to about 36 hours, from about 4 hours to about 24 hours, from about 4 hours to about 18 hours, from about 4 hours to about 12 hours, from about 4 hours to about 8 hours, from about 4 hours to about 6 hours from about 6 hours to about 48 hours, from about 6 hours to about 36 hours, from about 6 hours to about 24 hours, from about 6 hours to about 18 hours, from about 6 hours to about 12 hours, from about 6 hours to about 8 hours, from about 8 hours to about 48 hours, from about 8 hours to about 36 hours, from about 8 hours to about 24 hours, from about 8 hours to about 18 hours, from about 8 hours to about 12 hours, from about 12 hours to about 48 hours, from about 12 hours to about 36 hours, from about 12 hours to about 24 hours, from about 12 hours to about 18 hours, from about 18 hours to about 48 hours, from about 18 hours to about 36 hours, from about 18 hours to about 24 hours, from about 24 hours to about 48 hours, from about 24 hours to about 36 hours, or from about 36 hours to about 48 hours. In some embodiments, the rinsing and drying is performed at from about 18 hours to about 48 hours after the contacting. In some embodiments, the rinsing and drying is performed at about 24 hours after the contacting.

In some embodiments, the method of styling hair comprises straightening the hair or curling the hair. In some embodiments, the method of styling hair comprises straightening the hair. In some embodiments, the method of styling hair comprises curling the hair.

The present application further provides a method of styling hair, the method comprising:
(i) contacting the hair with a disentangling composition provided herein;
(ii) optionally heating the hair;
(iii) shaping the hair to a specific style;
(iv) contacting the hair with a crosslinking composition provided herein; and
(v) waiting a time sufficient to allow crosslinking.

In some embodiments, the shaping of step (iii) is performed using a styling tool. In some embodiments, the styling tool is selected from the group consisting of a heating tool, a shaping tool, and a heating and shaping tool. In some embodiments, the styling tool is selected from the group consisting of a flat iron, a curling iron, a hair dryer, a professional curling machine, an electric ceramic brush iron, and a curling wand. In some embodiments, the styling tool is a flat iron or a curling iron.

In some embodiments, the method further comprises rinsing and drying the hair after the shaping of step (iii) and before contacting of step (iv). In some embodiments, the rinsing and drying is performed after waiting a sufficient time after the shaping of step (iii). In some embodiments, the sufficient time is from about 1 to about 120 minutes, for example, from about 1 to 120, from about 1 to about 90, from about 1 to about 80, from about 1 to about 70, from about 1 to about 60, from about 1 to about 50, from about 1 to about 40, from about 1 to about 30, from about 1 to about 20, from about 1 to about 10, from about 1 to about 5, from about 1 to about 3, from about 3 to about 120, from about 3 to about 90, from about 3 to about 80, from about 3 to about 70, from about 3 to about 60, from about 3 to about 50, from about 3 to about 40, from about 3 to about 30, from about 3 to about 20, from about 3 to about 10, from about 3 to about 5, from about 5 to about 120, from about 5 to about 90, from about 5 to about 80, from about 5 to about 70, from about 5 to about 60, from about 5 to about 50, from about 5 to about 40, from about 5 to about 30, from about 5 to about 20, from about 5 to about 10, from about 10 to about 120, from about 10 to about 90, from about 10 to about 80, from about 10 to about 70, from about 10 to about 60, from about 10 to about 50, from about 10 to about 40, from about 10 to about 30, from about 10 to about 20, from about 20 to about 120, from about 20 to about 90, from about 20 to about 80, from about 20 to about 70, from about 20 to about 60, from about 20 to about 50, from about 20 to about 40, from about 20 to about 30, from about 30 to about 120, from about 30 to about 90, from about 30 to about 80, from about 30 to about 70, from about 30 to about 60, from about 30 to about 50, from about 30 to about 40, from about 40 to about 120, from about 40 to about 90, from about 40 to about 80, from about 40 to about 70, from about 40 to about 60, from about 40 to about 50, from about 50 to about 120, from about 50 to about 90, from about 50 to about 80, from about 50 to about 70, from about 50 to about 60, from about 60 to about 120, from about 60 to about 90, from about 60 to about 80, from about 60 to about 70, from about 70 to about 120, from about 70 to about 90, from about 70 to about 80, from about 80 to about 120, from about 80 to about 90 minutes, or from about 90 to about 120 minutes. In some embodiments, the sufficient time is from about 20 to about 45 minutes. In some embodiments, the sufficient time is from about 20 to 35 minutes. In some embodiments, the sufficient time is from about 1 to about 30 minutes.

In some embodiments, the drying after the shaping of step (iii) and before contacting of step (iv) is performed at from about 20 to about 90° C., for example, from about 20 to about 90° C., from about 20 to about 80° C., from about 20 to about 70° C., from about 20 to about 60° C., from about 20 to about 50° C., from about 20 to about 40° C., from about 20 to about 30° C., from about 30 to about 90° C., from about 30 to about 80° C., from about 30 to about 70° C., from about 30 to about 60° C., from about 30 to about 50° C., from about 30 to about 40° C., from about 40 to about 90° C., from about 40 to about 80° C., from about 40 to about 70° C., from about 40 to about 60° C., from about 40 to about 50° C., from about 50 to about 90° C., from about 50 to about 80° C., from about 50 to about 70° C., from about 50 to about 60° C., from about 60 to about 90° C., from about 60 to about 80° C., from about 60 to about 70° C., from about 70 to about 90° C., from about 70 to about 80° C., or from about 80 to about 90° C. In some embodiments, the drying is performed at from about 50° C. to about 80° C.

In some embodiments, the waiting of step (v) is from about 1 minute to about 90 minutes, for example, from about 1 to about 90, from about 1 to about 80, from about 1 to about 70, from about 1 to about 60, from about 1 to about 50, from about 1 to about 40, from about 1 to about 30, from about 1 to about 20, from about 1 to about 10, from about 1 to about 5, from about 1 to about 3, from about 3 to about 90, from about 3 to about 80, from about 3 to about 70, from about 3 to about 60, from about 3 to about 50, from about 3 to about 40, from about 3 to about 30, from about 3 to about 20, from about 3 to about 10, from about 3 to about 5, from about 5 to about 90, from about 5 to about 80, from about 5 to about 70, from about 5 to about 60, from about 5 to about 50, from about 5 to about 40, from about 5 to about 30, from about 5 to about 20, from about 5 to about 10, from about 10 to about 90, from about 10 to about 80, from about 10 to about 70, from about 10 to about 60, from about 10 to about 50, from about 10 to about 40, from about 10 to about 30, from about 10 to about 20, from about 20 to about 90, from about 20 to about 80, from about 20 to about 70, from about 20 to about 60, from about 20 to about 50, from about 20 to about 40, from about 20 to about 30, from about 30 to about 90, from about 30 to about 80, from about 30 to about 70, from about 30 to about 60, from about 30 to about 50, from about 30 to about 40, from about 40 to about 90, from about 40 to about 80, from about 40 to about 70, from about 40 to about 60, from about 40 to about 50, from about 50 to about 90, from about 50 to about 80, from about 50 to about 70, from about 50 to about 60, from about 60 to about 90, from about 60 to about 80, from about 60 to about 70, from about 70 to about 90, from about 70 to about 80, or from about 80 to about 90 minutes. In some embodiments, the waiting of step (v) is from about 1 minute to about 15 minutes. In some embodiments, the waiting of step (v) is from about 1 minute to about 5 minutes.

In some embodiments, the waiting of step (v) further comprises heating the hair. In some embodiments, the heating is performed at from about 50° C. to about 250° C., for example, from about 20 to about 250, from about 20 to about 230, from about 20 to about 210, from about 20 to about 190, from about 20 to about 170, from about 20 to about 150, from about 20 to about 130, from about 20 to about 110, from about 20 to about 90, from about 20 to about 70, from about 20 to about 50, from about 20 to about 30, from about 30 to about 250, from about 30 to about 230, from about 30 to about 210, from about 30 to about 190, from about 30 to about 170, from about 30 to about 150, from about 30 to about 130, from about 30 to about 110, from about 30 to about 90, from about 30 to about 70, from about 30 to about 50, from about 50 to about 250, from about 50 to about 230, from about 50 to about 210, from about 50 to about 190, from about 50 to about 170, from about 50 to about 150, from about 50 to about 130, from about 50 to about 110, from about 50 to about 90, from about 50 to about 70, from about 70 to about 250, from about 70 to about 230, from about 70 to about 210, from about 70 to about 190, from about 70 to about 170, from about 70 to about 150, from about 70 to about 130, from about 70 to about 110, from about 70 to about 90, from about 90 to about 250, from about 90 to about 230, from about 90 to about 210, from about 90 to about 190, from about 90 to about 170, from about 90 to about 150, from about 90 to about 130, from about 90 to about 110, from about 110 to about 250, from about 110 to about 230, from about 110 to about 210, from about 110 to about 190, from about 110 to about 170, from about 110 to about 150, from about 110 to about 130, from about 130 to about 250, from about 130 to about 230, from about 130 to about 210, from about 130 to about 190, from about 130 to about 170, from about 130 to about 150, from about 150 to about 250, from about 150 to about 230, from about 150 to about 210, from about 150 to about 190, from about 150 to about 170, from about 170 to about 250, from about 170 to about 230, from about 170 to about 210, from about 190 to about 250, from about 190 to about 230, from about 190 to about 210, from about 210 to about 250, from about 210 to about 230, or from about 230 to about 250° C. In some embodiments, the heating is performed at from about 100° C. to about 200° C. In some embodiments, the heating is performed at from about 150° C. to about 200° C. In some embodiments, the heating is performed at from about 50° C. to about 180° C. In some embodiments, the heating is performed at about 180° C.

In some embodiments, the method further comprises rinsing and drying the hair after step (v). In some embodiments, the rinsing and drying is performed at from about 30 minutes to about 48 hours after step (v), for example, at from about 30 minutes to about 48 hours, from about 30 minutes to about 36 hours, from about 30 minutes to about 24 hours, from about 30 minutes to about 18 hours, from about 30 minutes to about 12 hours, from about 30 minutes to about 8 hours, from about 30 minutes to about 6 hours, from about 30 minutes to about 4 hours, from about 30 minutes to about 2 hours, from about 30 minutes to about 1 hour, from about 1 hour to about 48 hours, from about 1 hour to about 36 hours, from about 1 hour to about 24 hours, from about 1 hour to about 18 hours, from about 1 hour to about 12 hours, from about 1 hour to about 8 hours, from about 1 hour to about 6 hours, from about 1 hour to about 4 hours, from about 1 hour to about 2 hours, from about 2 hours to about 48 hours, from about 2 hours to about 36 hours, from about 2 hours to about 24 hours, from about 2 hours to about 18 hours, from about 2 hours to about 12 hours, from about 2 hours to about 8 hours, from about 2 hours to about 6 hours, from about 2 hours to about 4 hours, from about 4 hours to about 48 hours, from about 4 hours to about 36 hours, from about 4 hours to about 24 hours, from about 4 hours to about 18 hours, from about 4 hours to about 12 hours, from about 4 hours to about 8 hours, from about 4 hours to about 6 hours from about 6 hours to about 48 hours, from about 6 hours to about 36 hours, from about 6 hours to about 24 hours, from about 6 hours to about 18 hours, from about 6 hours to about 12 hours, from about 6 hours to about 8 hours, from about 8 hours to about 48 hours, from about 8 hours to about 36 hours, from about 8 hours to about 24 hours, from about 8 hours to about 18 hours, from about 8 hours to about 12 hours, from about 12 hours to about 48 hours, from about 12 hours to about 36 hours, from about 12 hours to about 24 hours, from about 12 hours to about 18 hours, from about 18 hours to about 48 hours, from about 18 hours to about 36 hours, from about 18 hours to about 24 hours, from about 24 hours to about 48 hours, from about 24 hours to about 36 hours, or from about 36 hours to about 48 hours. In some embodiments, the rinsing and drying is performed at from about 18 hours to about 48 hours after step (v). In some embodiments, the rinsing and drying is performed at about 24 hours after step (v).

In some embodiments, the method of styling hair comprises straightening the hair or curling the hair. In some embodiments, the method of styling hair comprises straightening the hair. In some embodiments, the method of styling hair comprises curling the hair.

In some embodiments, the methods provided herein are performed on a subject (e.g., a method of styling the hair of a subject; a method of straightening the hair of a subject; a method of curling the hair of the subject, and the like). As used herein, the term "subject," refers to any animal, including mammals. Example subjects include, but are not limited to, humans, dogs, cats, and horses. In some embodiments, the subject is a human. In some embodiments, the subject is a dog or a cat.

Combination Treatments

In some embodiments, the compositions provided herein may be used in combination with one or more additional treatments (e.g., one or more additional hair styling treatments). Example treatments include, but are not limited to, shampoos, conditioners, hair bleaching agents, hair coloring agents (e.g., dyes), hair styling agents (e.g., hairspray, gel, cream, mousse, etc.), hair styling tools (e.g., flat iron, curling iron, and the like), hair cutting tools (e.g., scissors, electric clippers, and the like), and hair coloring tools (e.g., brushes, applicators, foil wraps, and the like).

Kits

The present application further provides a kit comprising a disentangling composition as described herein, a crosslinking composition as described herein, and instructions for preparing and using the compositions described herein.

In some embodiments, the kit comprises one or more components of the compositions provided herein (e.g., one or more components of a disentangling composition or one or more components of a crosslinking composition). For example, the components can be separately packaged or contained. In some embodiments, the kit comprises:

(i) one or more of the independently selected reducing agents provided herein;

(ii) one or more of the independently selected disentangling agents provided herein;

(iii) one or more of the independently selected polycarboxylic acids provided herein;

(iv) one or more of the independently selected alkali metal hypophosphites provided herein;

(v) one or more of the independently selected crosslinking agents provided herein; and (vi) instructions for using the kit.

In some embodiments, the instructions comprise instructions for mixing the one or more independently selected reducing agents and one or more independently selected disentangling agents to form a disentangling composition provided herein. In some embodiments, the instructions comprise instructions for mixing the one or more independently selected polycarboxylic acids, the one or more independently selected alkali metal hypophosphites, and the one or more independently selected crosslinking agents to form a crosslinking composition provided herein. In some embodiments, the instructions comprise instructions for performing a method provided herein (e.g., a method of styling hair).

In some embodiments, the kit comprises a disentangling composition provided herein and instructions for using the kit. In some embodiments, the instructions comprise instructions for performing a method provided herein (e.g., a method of styling hair). In some embodiments, the kit comprises a crosslinking composition provided herein and instructions for using the kit. In some embodiments, the instructions comprise instructions for performing a method provided herein (e.g., a method of styling hair).

In some embodiments, the kit comprises:

(i) a disentangling composition provided herein;

(ii) a crosslinking composition provided herein; and (iii) instructions for using the kit.

In some embodiments, the instructions comprise instructions for performing a method provided herein (e.g., a method of styling hair).

In some embodiments, the kits provided herein further comprise one or more additional hair styling treatments. In some embodiments, the kits further comprise one or more additional treatments each independently selected from the group consisting of shampoo, conditioner, and hair dye.

In some embodiments, the kits provided herein further comprise one or more additional hair styling tools. In some embodiments, the kits further comprise one or more hair styling tools each independently selected from the group consisting of a hair styling tool (e.g., flat iron, curling iron, and the like), a hair cutting tool (e.g., scissors, electric clippers, and the like), and a hair coloring tool (e.g., brush, applicator, foil wraps, and the like).

EXAMPLES

The invention is further described in the following examples, which do not limit the scope of the invention described in the claims.

General Methods

For hair straightening, the quantitative parameter used to evaluate the curliness of hair was the degree of straightening (% C) calculated according to equation (1):

$$\% \, C = \frac{L_0}{L_s} \times 100\% \qquad \text{Equation (1)}$$

wherein, $L_0$ is the length of hair without tension, and $L_s$ is the length of completely straightened hair. The % C ranges from 0 to 100%, representing transition of hair from extensively curly/kinky to straight. In hair straightening, the higher the % C is, the better the straightening effect is.

For hair curling, the quantitative parameter used to evaluate the curliness of hair was the degree of curling (% E) calculated according to equation (2):

$$\% \, E = \frac{N_0}{N_c} \times 100\% \qquad \text{Equation (2)}$$

wherein, $N_0$ is number of circles per unit length without tension after heating and washing, and $N_c$ is theoretical number of circles on the rod per unit length without tension before heating. The % E ranges from 0 to 100%, representing transition of hair from straight to extensively curly/kinky. In hair curling, the higher the % E is, the better the curling effect is.

Manual Hair Washing Method

About 3% w/w of shampoo was added into water, which was heated to 50° C. A tress of hair was added into the solution and manually washed for 10 min. The hair-to-liquor ratio was 1:20. The tress of hair was rinsed for 5 times in distilled water at 50° C. The hair-to-liquor ratio was 1:200.

Example 1. 2-(2-aminoethoxy)ethanol as the Dis-Entangling Agent and the Crosslinking Booster. Hair Straightening Via Dis-Entanglement of Keratin Molecular Structures Assisted with Ethanolamines and Crosslinking Boosted with Alkanolamines A tress of curling hair was forced to be straightened, soaked in dis-entangling solution containing 0.4 mol/L of cysteine and 0.47 mol/L of 2-(2-aminoethoxy)ethanol with pH adjusted to 9.5 using sodium hydroxide. The liquor ratio was 1:100, and the treatment was carried out at 50° C. for 25 min. Subsequently, the tress of hair was rinsed in distilled water to remove the disentangling agent. One end of the hair tress was fixed on a frame and the other end was connected to a clamp to force the hair straight.

Figure 1B:
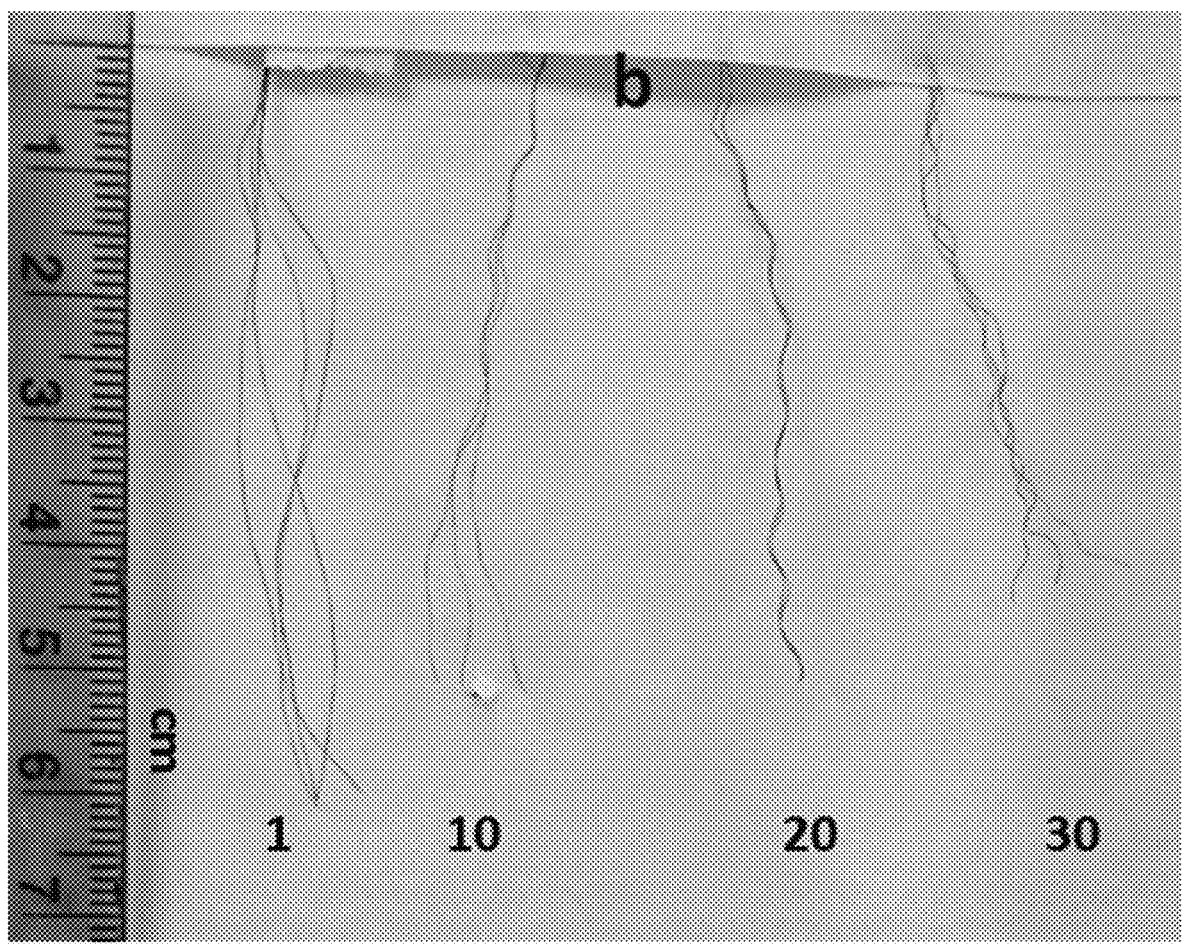
FIG. 1b shows digital photos representative of straightened curly hair after 1, 10, 20, and 30 wash cycles.

Crosslinking solution containing 1.04 mol/L of citric acid, 0.94 mol/L of sodium hypophosphite (SHP) and 1.04 mol/L of 2-(2-aminoethoxy)ethanol was applied onto the hair tress to achieve % pick-up of 105%. The straightened hair with crosslinking solution was dried at 80° C. for 30 min to remove water, and then cured at 180° C. for 3 min to complete crosslinking. After conditioned in air for 1440 min, the dried hair tress was rinsed in distilled water twice to remove remaining chemicals. The hair tress was then dried in the ambient environment. To evaluate durability of the straightening effects, the hair tress was manually washed using commercial shampoo and conditioner for 1-30 times. The hair tress after each wash cycle was measured for its % C. The results are shown in FIGS. 1a-1b. It could be found that the % C was 90% after the first wash cycle, and retained 67% after 30 wash cycles. The lower the % C was, the curvier the hair appeared as shown in FIG. 1b.

Example 2. Sodium Dodecyl Sulfate (SDS) as the Dis-Entangling Agent and Glycerol as the Crosslinking Booster. Hair Straightening Via Dis-Entanglement of Keratin Molecular Structures Assisted with Surfactants and Crosslinking Boosted with Polyhydryl Alcohols A tress of curling hair was soaked in disentangling solution containing 0.4 mol/L of cysteine and 0.173 mol/L of SDS with pH adjusted to 9.5 using sodium hydroxide. The liquor ratio was 1:100, and the treatment was carried out at 50° C. for 25 min. Subsequently, the hair tress was rinsed in distilled water to remove the disentangling agent. One end of the hair tress was fixed on a frame and the other end was connected to a clamp to force the hair straight.

Figure 2:
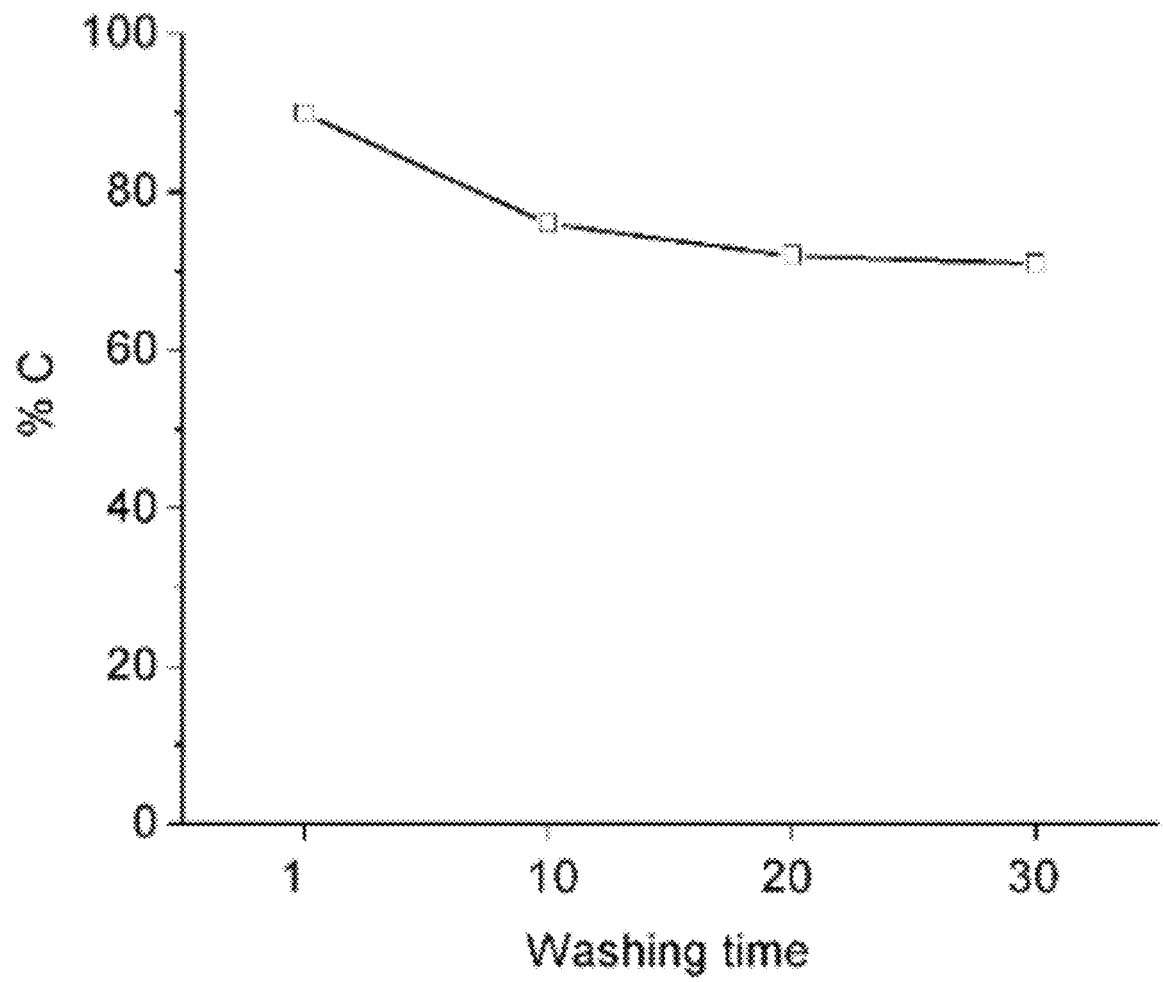
FIG. 2 shows the effect of washing times on the % C of the straightened curly hair using sodium dodecyl sulfate (SDS) as dis-entangling agent.

Crosslinking solution containing 1.04 mol/L of citric acid, 0.94 mol/L of sodium hypophosphite (SHP) and 0.624 mol/L of glycerol was applied onto the hair tress to achieve % pick-up of 100%. The straightened hair with crosslinking solution was then dried at 80° C. for 30 min to remove water, and then cured at 180° C. for 3 min to complete crosslinking. After conditioned in air for 1440 min, the dried hair tress was rinsed in distilled water twice to remove remaining chemicals. The hair tress was then dried in the ambient environment. To evaluate durability of the straightening effects, the hair tress was manually washed using commercial shampoo and conditioner for 1-30 times. The hair tress from each wash cycle was measured for its % C. The results are shown in FIG. 2. It could be found that the % C was 90% after the first wash cycle, and retained 71% after 30 wash cycles.

Example 3. Dimethylacetamide (DMAc) as the Dis-Entangling Agent and Lysine as the Crosslinking Booster. Hair Straightening Via Dis-Entanglement of Keratin Molecular Structures Assisted with Amides and Crosslinking Boosted with Alkanolamines A tress of curling hair was soaked in disentangling solution containing 0.4 mol/L of cysteine and 0.57 mol/L of DMAc with pH adjusted to 9.5 using sodium hydroxide. The liquor ratio was 1:100, and the treatment was carried out at 50° C. for 25 min. Subsequently, the hair tress was rinsed in distilled water to remove the disentangling agent. One end of the hair tress was then fixed on a frame and the other end was connected to a clamp to force the hair straight.

Figure 3:
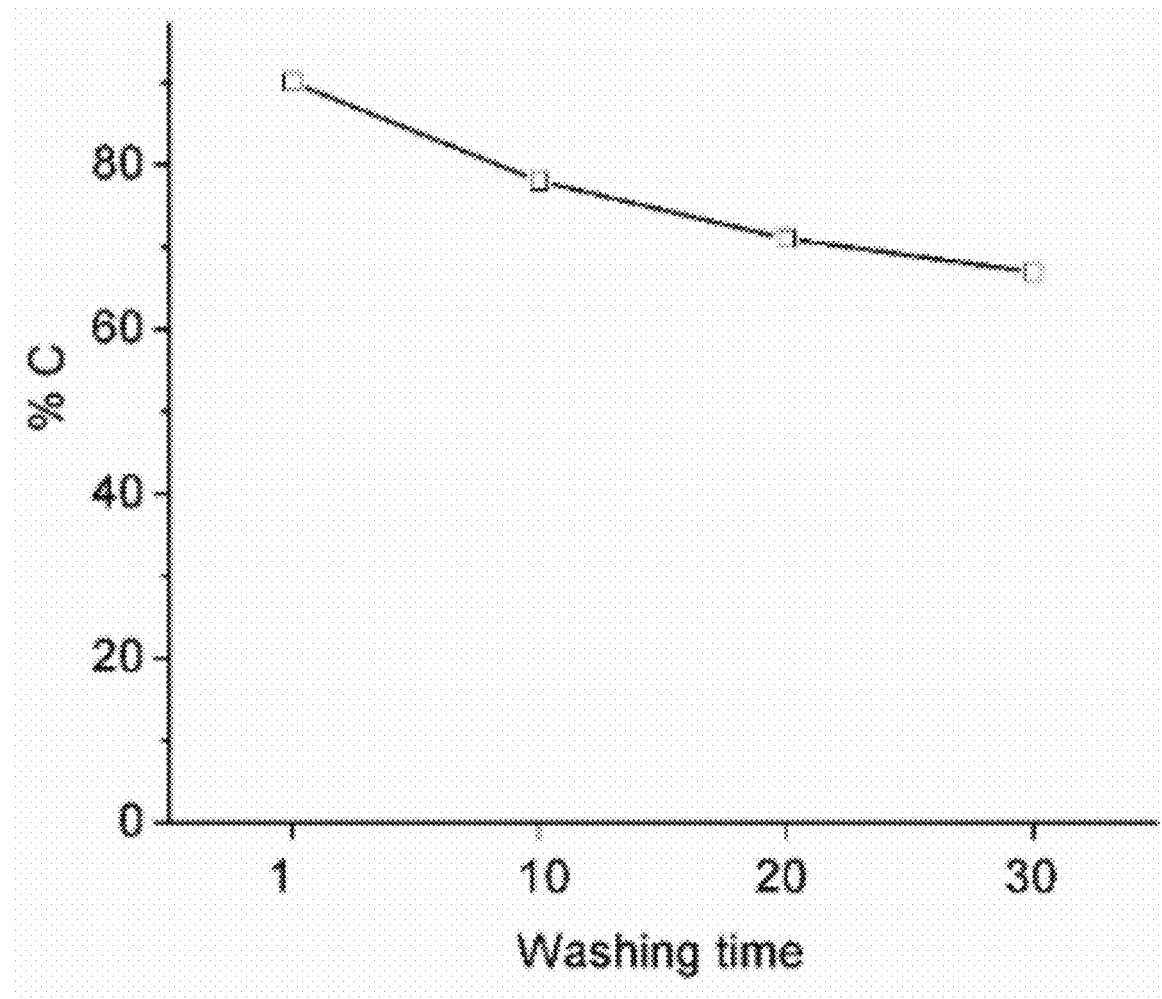
FIG. 3 shows the effect of washing times on the % C of the straightened curly hair using DMAc as dis-entangling agent and lysine as crosslinking booster.

Crosslinking solution containing 1.04 mol/L of citric acid, 0.94 mol/L of sodium hypophosphite (SHP) and 1.04 mol/L of lysine was applied onto the hair tress to achieve % pick-up of 105%. The straightened hair with crosslinking solution was dried at 80° C. for 30 min to remove water, and then cured at 180° C. for 3 min to complete crosslinking. After conditioned in air for 1440 min, the dried hair tress was rinsed in distilled water twice to remove remaining chemicals. The hair tress was then dried in the ambient environment. To evaluate durability of the straightening effects, the hair tress was manually washed using commercial shampoo and conditioner for 1-30 times. The hair tress from each wash cycle was measured for its % C. The results are shown in FIG. 3. It could be found that the % C was 90% after the first wash cycle, and retained 67% after 30 wash cycles.

Example 4. Ethyl Acetate as the Dis-Entangling Agent and Mannitol as the Crosslinking Booster. Hair Straightening Via Dis-Entanglement of Keratin Molecular Structures Assisted with Esters and Crosslinking Boosted with Polyhydryl Alcohols A tress of curling hair was soaked in disentangling solution containing 0.4 mol/L of cysteine and 0.57 mol/L of ethyl acetate with pH adjusted to 9.5 using sodium hydroxide. The liquor ratio was 1:100, and the treatment was carried out at 50° C. for 25 min. Subsequently, the hair tress was rinsed in distilled water to remove the disentangling agent. One end of the hair tress was then fixed on a frame and the other end was connected to a clamp to force the hair straight.

Figure 4:
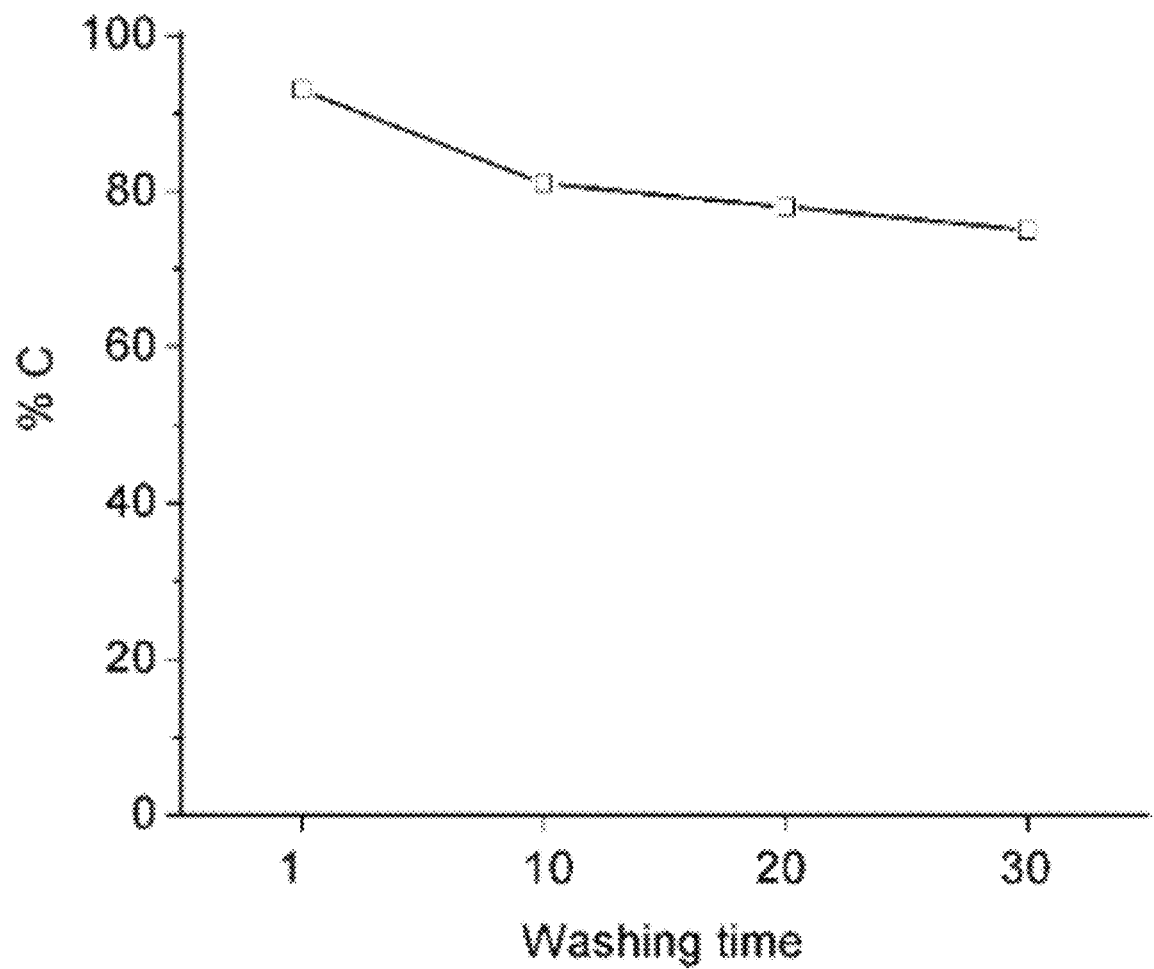
FIG. 4 shows the effect of washing times on the % C of the straightened curly hair using ethyl acetate as dis-entangling agent and mannitol as crosslinking booster.

Crosslinking solution containing 1.04 mol/L of citric acid, 0.94 mol/L of sodium hypophosphite (SHP) and 0.624 mol/L of mannitol was applied onto the hair tress to achieve % pick-up of 100%. The straightened hair with crosslinking solution was dried at 80° C. for 30 min to remove water, and then cured at 180° C. for 3 min to complete crosslinking. After conditioned in air for 1440 min, the dried hair tress was rinsed in distilled water twice to remove remaining chemicals. The hair tress was then dried in the ambient environment. To evaluate durability of the straightening effects, the hair tress was manually washed using commercial shampoo and conditioner for 1-30 times. The hair tress from each wash cycle was measured for its % C. The results are shown in FIG. 4. It could be found that the % C was 93% after the first wash cycle, and retained 75% after 30 wash cycles.

Example 5: 2-(2-aminoethoxy)ethanol as the Dis-Entangling Agent and Lysine as the Crosslinking Booster. Hair Curling Via Dis-Entanglement of Keratin Molecular Structures Assisted with Ethanolamines and Crosslinking Boosted with Amino Acids A tress of straight hair was soaked in disentangling solution containing 0.4 mol/L of cysteine and 0.31 mol/L of 2-(2-aminoethoxy)ethanol with pH adjusted to 9.5 using sodium hydroxide. The liquor ratio was 1:100, and the treatment was carried out at 50° C. for 25 min. Subsequently, the tress of hair was wound onto a glass rod with diameter of 7 mm. Both ends of the tress were fixed on the rod with tapes. The tress of hair on the rod was rinsed in distilled water to remove disentangling solution sorbed in the hair.

Figure 5A:
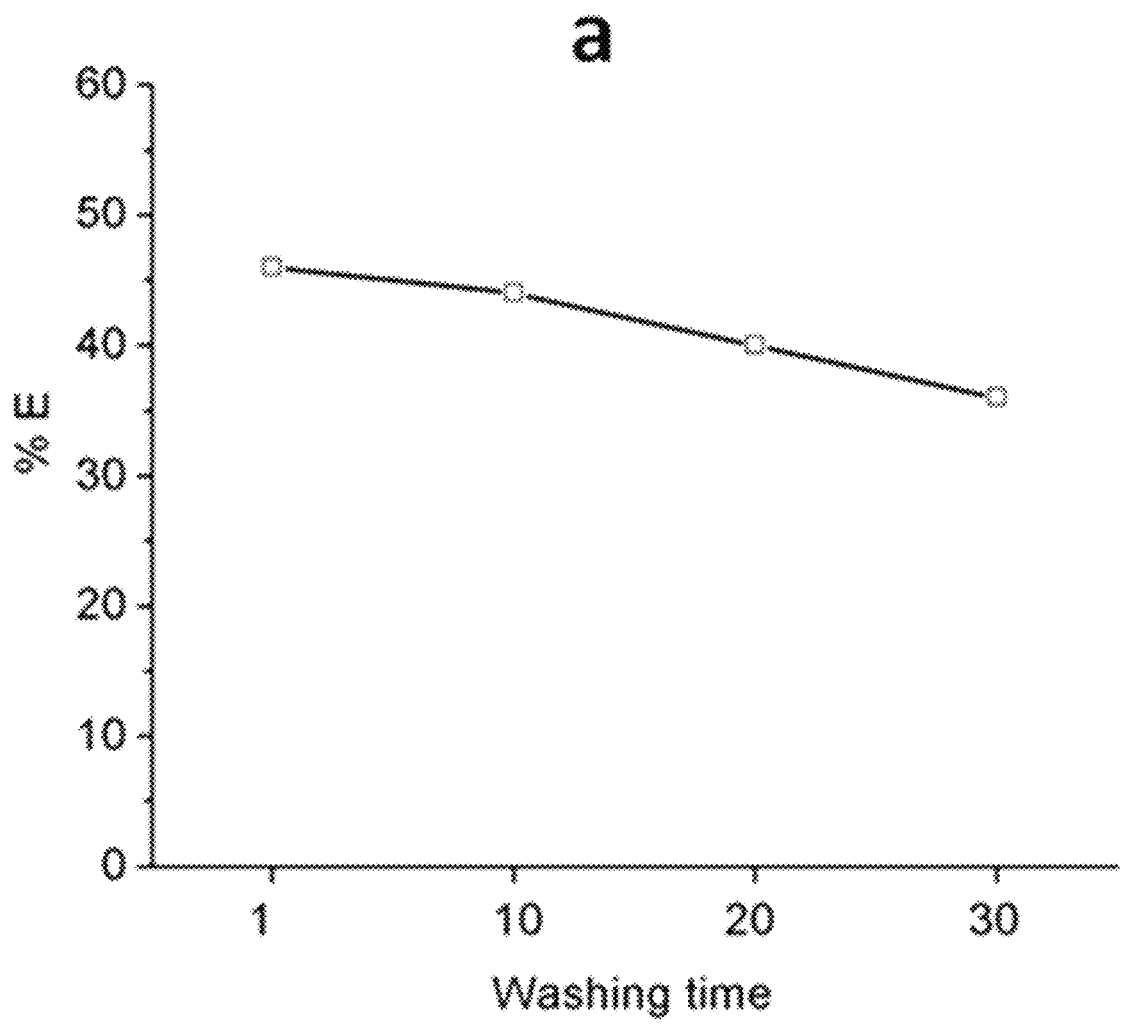
FIG. 5a shows the effect of washing times on the % E of the curled straight hair using 2-(2-aminoethoxy)ethanol as dis-entangling agent and lysine as crosslinking booster.
Figure 5B:
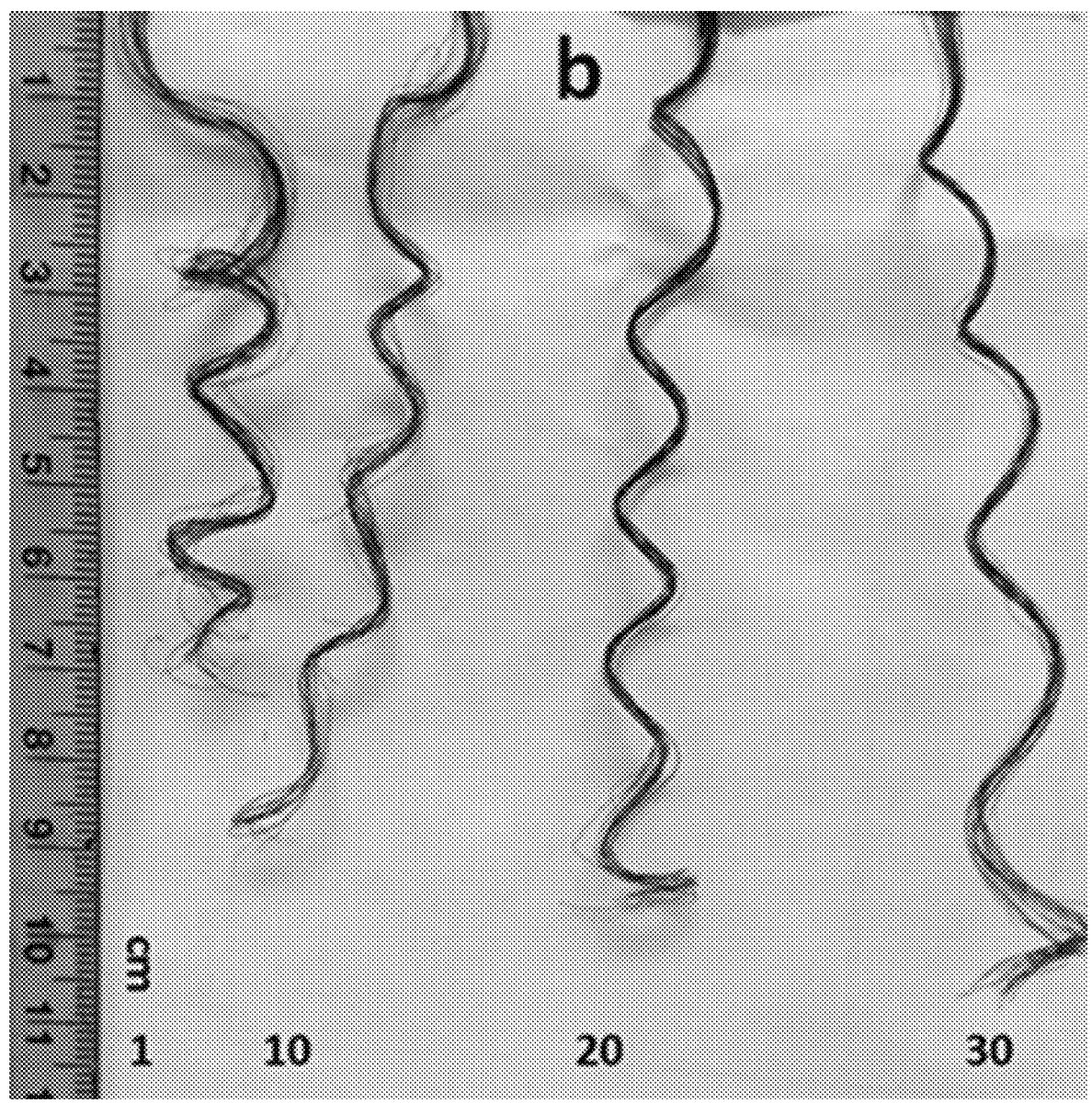
FIG. 5b shows digital photos representative of curled straight hair after 1, 10, 20, and 30 wash cycles.

Crosslinking solution containing 1.04 mol/L of citric acid, 0.94 mol/L of sodium hypophosphite (SHP) and 1.04 mol/L of lysine was applied onto the hair tress to achieve % pick-up of 100%. The curled hair with crosslinking solution was dried under 80° C. for 20 min to remove water, and then treated at 180° C. for 3 min to complete crosslinking. 1440 min after crosslinking, the dried hair tress was rinsed in distilled water for 2 times to remove any remaining chemicals. The hair tress was then dried in the ambient environment. To evaluate the durability of the curling effects, the hair tress was manually washed using commercial shampoo and conditioner, 10 times. The hair tress from each wash cycle was measured for its % E. The results are shown in FIG. 5*a*. The % E decreased from 46% after the first wash cycle to 36% after 30 wash cycles. The tress of hair remained wavy after 30 wash cycles, as shown in FIG. 5*b*.

Example 6: Dimethylacetamide (DMAc) as the Dis-Entangling Agent and Lysine as the Crosslinking Booster. Hair Curling Via Dis-Entanglement of Keratin Molecular Structures Assisted with Amides and Crosslinking Boosted with Amino Acids A tress of straight hair was soaked in disentangling solution containing 0.4 mol/L of cysteine and 0.3 mol/L of DMAc with pH adjusted to 9.5 using sodium hydroxide. The liquor ratio was 1:100, and the treatment was carried out at 50° C. for 25 min. Subsequently, the tress of hair was wound onto a glass rod with diameter of 7 mm. Both ends of the tress were fixed on the rod with tapes. The tress of hair on the rod was rinsed in distilled water to remove disentangling solution sorbed in the hair.

Figure 6A:
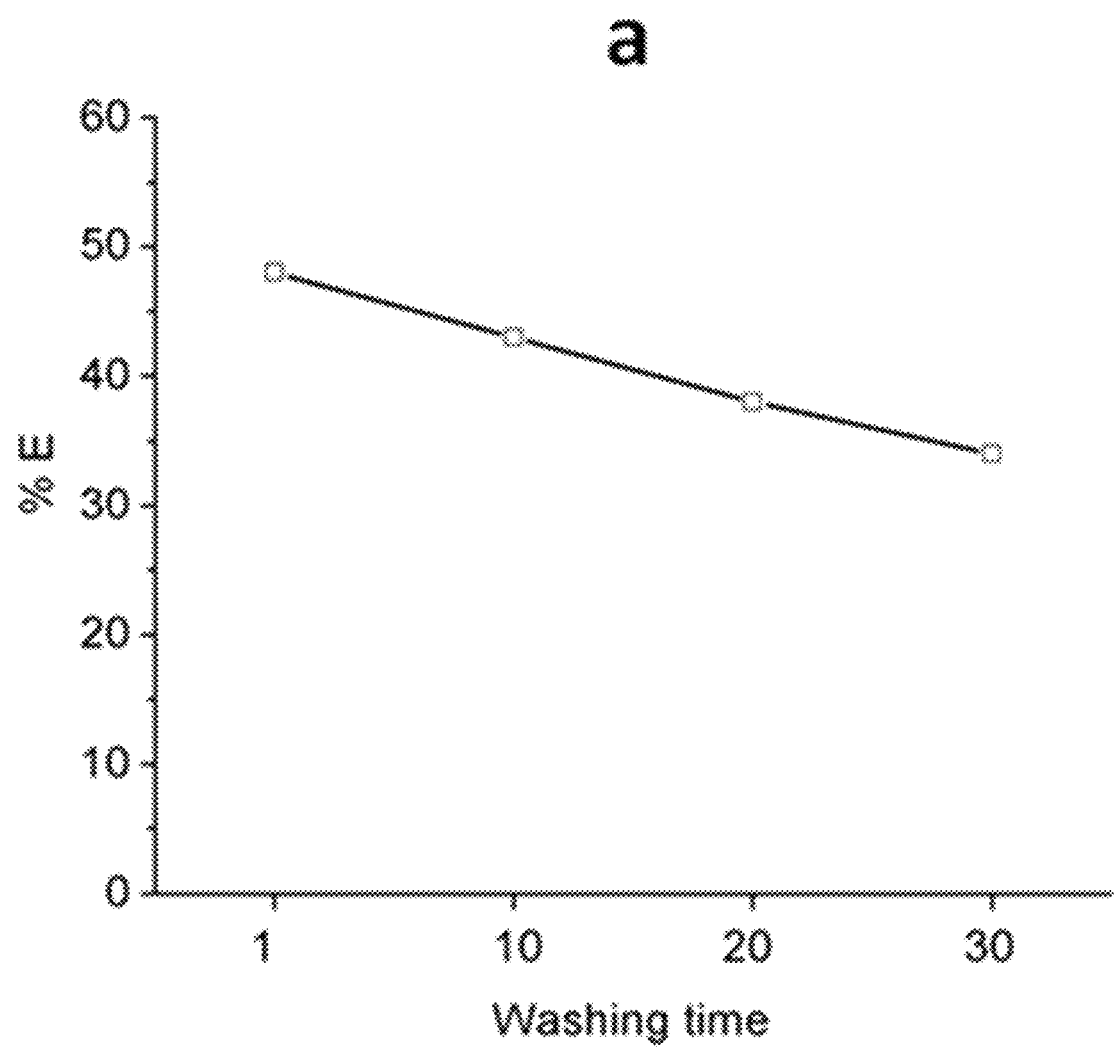
FIG. 6a shows the effect of washing times on the % E of the curled straight hair using DMAc as the dis-entangling agent and lysine as the crosslinking booster.
Figure 6B:
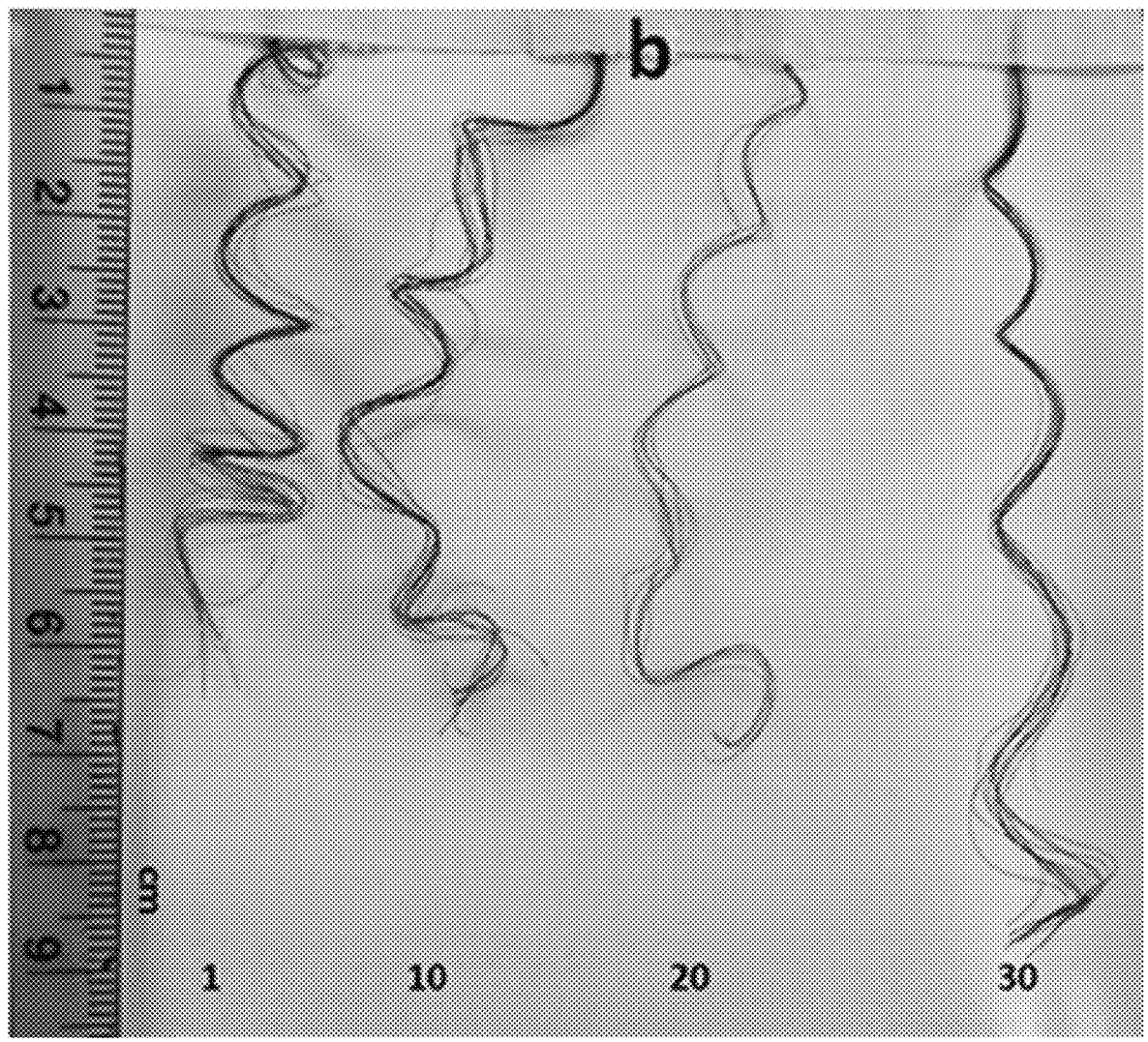
FIG. 6b shows digital photos representative of curled straight hair after 1, 10, 20, and 30 wash cycles.

Crosslinking solution containing 1.04 mol/L of citric acid, 0.94 mol/L of sodium hypophosphite (SHP) and 0.624 mol/L of lysine was applied onto the hair tress to achieve % pick-up of 100%. The curled hair with crosslinking solution was dried under 80° C. for 20 min to remove water, and then treated at 180° C. for 3 min to complete crosslinking. About 1440 min after crosslinking, the dried hair tress was rinsed in distilled water for 2 times to remove any remaining chemicals. The hair tress was then dried in the ambient environment. To evaluate the durability of the curling effects, the hair tress was manually washed using commercial shampoo and conditioner for 1-30 times. The hair tress from each wash cycle was measured for its % E. The results are shown in FIG. 6a. The % E decreased from 48% after the first wash cycle to 34% after 30 wash cycles. The tress of hair remained wavy after 30 wash cycles as shown in FIG. 6b.

Example 7: Ethyl Acetate as the Dis-Entangling Agent and Lysine as Crosslinking Booster. Hair Curling Via Dis-Entanglement of Keratin Molecular Structures Assisted with Esters and Crosslinking Boosted with Amino Acids A tress of straight hair was soaked in disentangling solution containing 0.4 mol/L of cysteine and 0.57 mol/L of ethyl acetate with pH adjusted to 9.5 using sodium hydroxide. The liquor ratio was 1:100, and the treatment was carried out at 50° C. for 25 min. Subsequently, the tress of hair was wound onto a glass rod with diameter of 7 mm. Both ends of the tress were fixed on the rod with tapes. The tress of hair on the rod was rinsed in distilled water to remove disentangling solution sorbed in the hair.

Figure 7A:
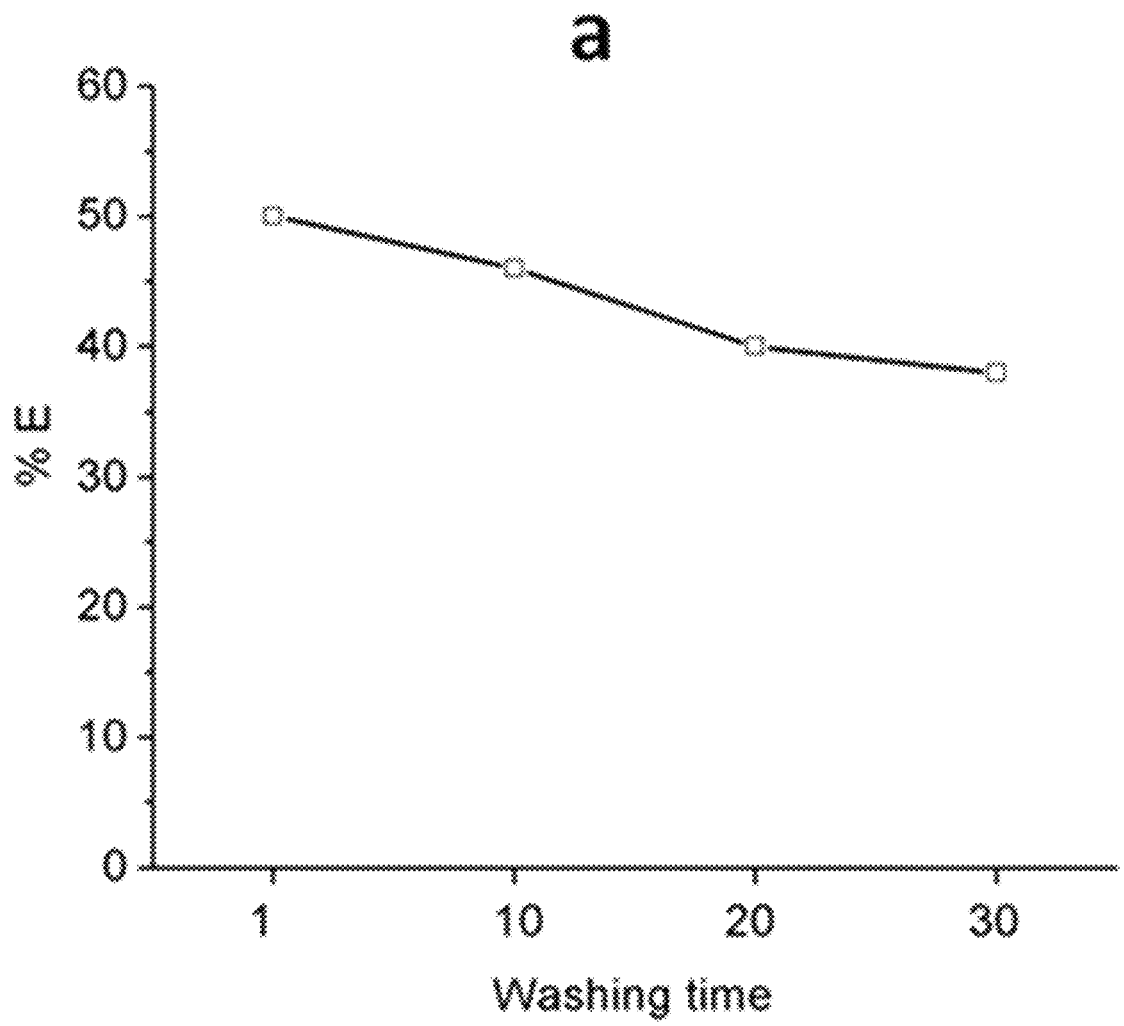
FIG. 7a shows the effect of washing times on the % E of the curled straight hair using ethyl acetate as dis-entangling agent and lysine as crosslinking booster.
Figure 7B:
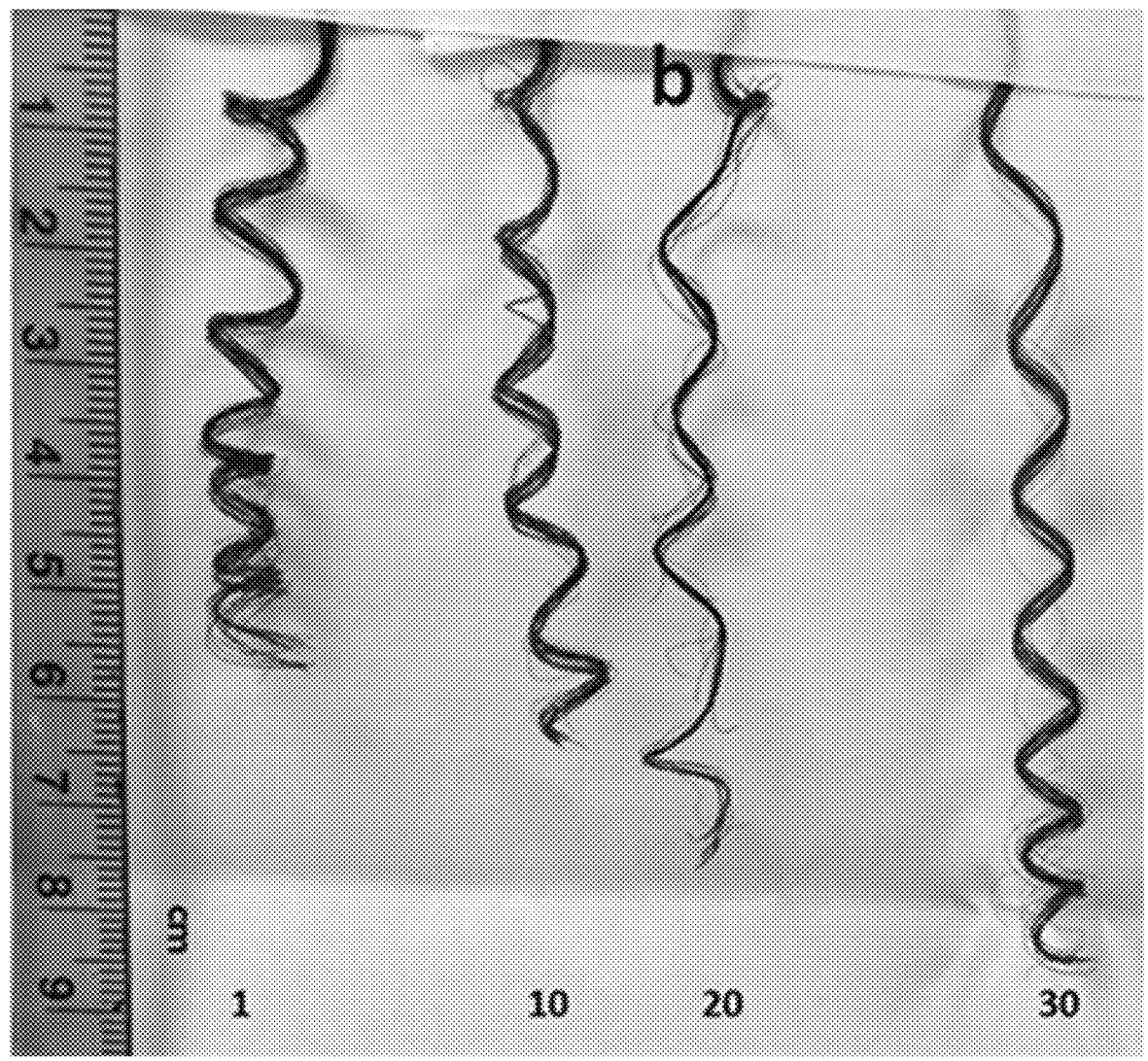
FIG. 7b shows digital photos representative of curled straight hair after 1, 10, 20, and 30 wash cycles.

Crosslinking solution containing 1.04 mol/L of citric acid, 0.94 mol/L of sodium hypophosphite (SHP) and 1.04 mol/L of lysine was applied onto the hair tress to achieve % pick-up of 100%. The curled hair with crosslinking solution was dried under 80° C. for 20 min to remove water, and then treated at 180° C. for 3 min to complete crosslinking. About 1440 min after crosslinking, the dried hair tress was rinsed in distilled water twice to remove any remaining chemicals. The hair tress was then dried in the ambient environment. To evaluate the durability of the curling effects, the hair tress was manually washed using commercial shampoo and conditioner for 1-30 times. The hair tress from each wash cycle was measured for its % E. The results are shown in FIG. 7a. The % E decreased from 50% after the first wash cycle to 38% after 30 wash cycles, indicating gradual straightening of curled hair. The tress of hair remained wavy after 30 wash cycles as shown in FIG. 7b.

Example 8. Urea as the Dis-Entangling Agent and 1,2,3,4-Butanetetrol as the Crosslinking Booster. Hair Curling Via Dis-Entanglement of Keratin Molecular Structures Assisted with Amides and Crosslinking Boosted with Polyhydryl Alcohols A tress of straight hair was soaked in dis-entangling solution containing 0.4 mol $L^{-1}$ of cysteine and 2 mol $L^{-1}$ of urea with pH adjusted to 9.5 using sodium carbonate. The treatment was carried out at 50° C. for 25 min with liquor ratio of 1:100. Subsequently, the tress of hair was wound onto a glass rod with diameter of 7 mm. Both ends of the tress were fixed on the rod with tapes. The tress of hair on the rod was rinsed in distilled water to remove dis-entangling solution sorbed in the hair.

Crosslinking solution containing 1.04 mol $L^{-1}$ of citric acid, 0.94 mol $L^{-1}$ of sodium hypophosphite (SHP) and 0.728 mol $L^{-1}$ of 1,2,3,4-butanetetrol was applied onto the hair tress to achieve % pick-up of 100%. The curled hair with citric acid, SHP and 1,2,3,4-butanetetrol was dried under 80° C. for 20 min to remove water, and then treated at 180° C. for 3 min to complete crosslinking. About 1440 min after crosslinking, the dried hair tress was rinsed in distilled water twice to remove any remaining chemicals. The hair tress was then dried in the ambient environment. After manual washing using commercial shampoo and conditioner for 30 times, the hair tress showed % E of 70%, % retention of dry tensile strength and % elongation of 76% and 120%, respectively, and % retention of wet tensile strength and % elongation of 64% and 129%, respectively.

Figure 8:
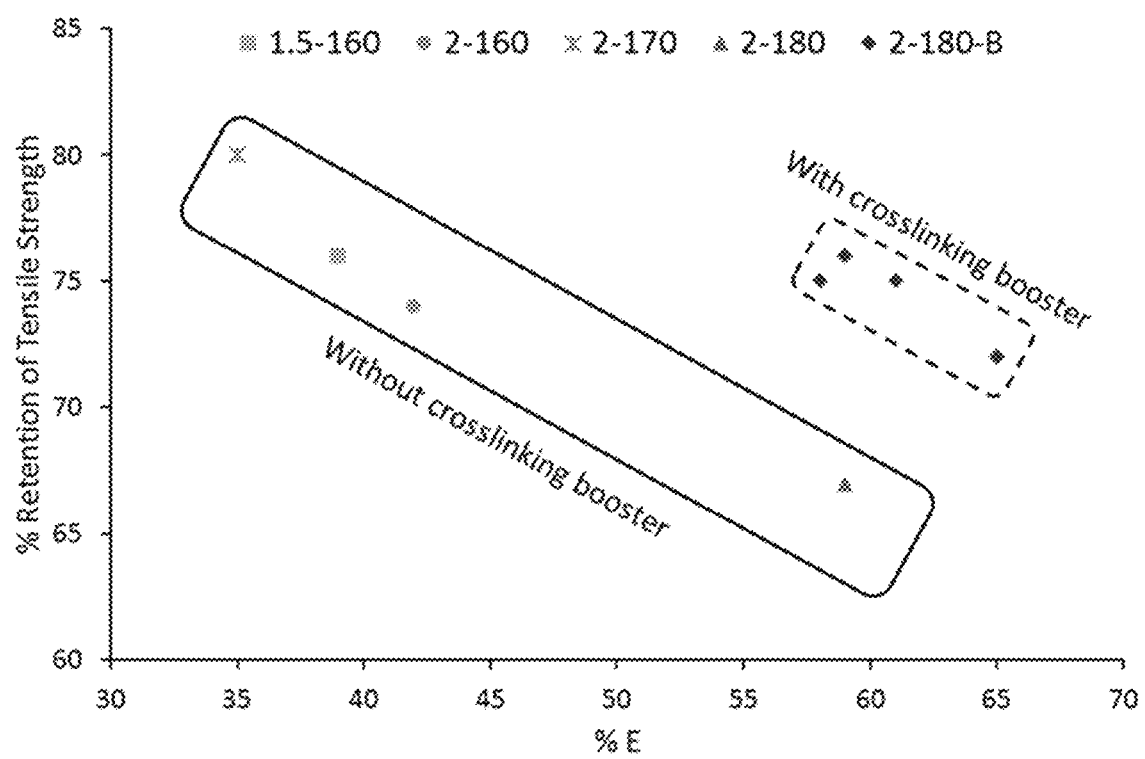
FIG. 8 shows % E and retention of tensile strength of hair curling conducted under different conditions. The condition parameters studied included concentration of carbamide (i.e., urea) as a dis-entangling agent, existence of crosslinking booster and crosslinking temperature. For example, the figure legend 1.5-160 refers to 1.5 M carbamide and crosslinking temperature of 160° C. The letter "B" in the figure legend indicates utilization of booster for crosslinking.

Example 9: Relationship Between % E and % Retention of Tensile Strength of Curled Straight Hair FIG. 8 shows the % E and % retention of tensile strength of hair curling conducted under different conditions. In general, when % E increased, retention of tensile strength decreased due to more damage of keratin backbones under the harsher conditions for either reduction or crosslinking. However, once the crosslinking booster was applied in the second step, the % E and retention of tensile strength increased simultaneously. The boosting effect could be further enhanced if more hydroxyl groups existed per carbon in the 4-carbon crosslinking booster. Here, comparing to 1,4-butanediol and 1,2,4-butantriol, 1,2,3,4-butanetetrol showed the best boosting effect for the crosslinking, and consequently, the best curling effect, retention of tensile strength of hair.

Example 10. Product Comparison

Effects of straightening and curling methods in this invention on the tensile properties of hair were evaluated and compared with that of commercial products. We used 4 to 5 commercial products for hair curling and 4 to 5 commercial products for hair straightening to treat straight hair and curly hair, respectively. The products under optimal conditions with the best straightening and curling effects were used as controls.

Table 1 indicates that the straightening method of Example 1 has better straightening effect than the commercial straightening product. The two approaches showed similar retention of tensile strength and slightly lower strain retention.

TABLE 1

Comparison of % C, retention of tensile strength and strain among the commercial straightening product and methods used in example 1 after 10 times of washing.

|  | Commercial straightening product | Example 1 |
|---|---|---|
| % C | 60% | 75% |
| Retention of tensile strength | 50% | 46% |
| Retention of tensile strain | 110% | 95% |

Table 2 indicates that the curling method in Examples 6 and 7 have better curling effect, retention of tensile strength and slightly lower strain retention, compared to the commercial curling product.

TABLE 2

Comparison of % E, retention of tensile strength and strain among the commercial curling product and methods used in Examples 6 and 7.

|  | Commercial curling product | Example 6 | Example 7 |
|---|---|---|---|
| % E | 44% | 48% | 50% |
| Retention of tensile strength | 80% | 87% | 86% |
| Retention of tensile strain | 126% | 111% | 100% |

Example 11. Urea as the Dis-Entangling Agent and Oxidized Sucrose as Crosslinking Agent. Hair Curling Via Dis-Entanglement of Keratin Helical Structures Assisted with Urea and Crosslinking Using Oxidized Sucrose A tress of straight hair of 0.1 g was soaked in dis-entangling solution containing 0.083 mol L$^{-1}$ of cysteine and 2 mol L$^{-1}$ of urea with pH adjusted to 9.5 using sodium carbonate. The treatment was carried out at 60° C. for 30 min with liquor ratio of 1:100. Subsequently, the tress of hair was wound onto a glass rod with diameter of 7 mm. Both ends of the tress were fixed on the rod with tapes. The tress of hair on the rod was rinsed in distilled water to remove dis-entangling solution sorbed in the hair. A second tress of 0.1 g straight hair with the same length was wounded onto another glass rod with the same diameter for crosslinking as comparison. The second tress of hair was not treated with a dis-entangling solution.

Figure 9:
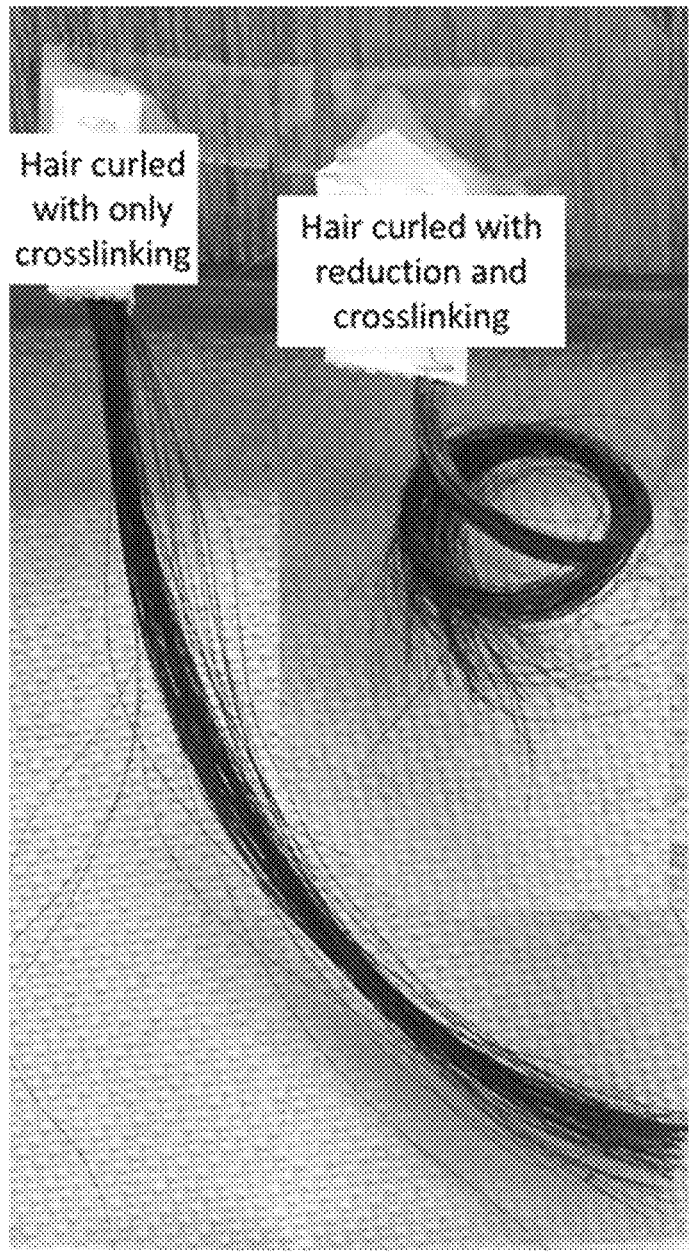
FIG. 9 shows the effect of washing times on the % E of the curled straight hair using urea as the dis-entangling agent and oxidized sucrose as the crosslinking agent. Left: Tress of hair curled with only the crosslinking solution. Right: Tress of hair curled with the dis-entangling and crosslinking solutions. Both hair tresses are shown after 20 wash cycles.

Both tresses of hair were then individually soaked in 20 g of crosslinking solution containing 0.0015 mol L$^{-1}$ oxidized sucrose, heated under 60° C. for 1 h, and then rinsed in distilled water twice. The hair tresses were then dried in ambient environment. After manual washing using commercial shampoo and conditioner for 20 times, the hair tress treated with the dis-entangling and crosslinking solutions showed % E of 65%, % retention of dry tensile strength of 91%, and % elongation of 100%, while the hair tress which was not soaked in the dis-entangling solution did not retain curly appearance, as shown in FIG. 9.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of styling hair, comprising:
   (i) contacting the hair with a first composition consisting of:
      (a) a reducing agent, wherein the reducing agent consists of cysteine;
      (b) one or more independently selected disentangling agents; and
      (c) a solvent selected from the group consisting of methanol, ethanol, isopropanol, and water;
         wherein each of the one or more independently selected disentangling agents is selected from the group consisting of an alkanolamine, an amine, an amide, an alcohol, an amino acid, a surfactant, an anhydride, a guanidinium salt, an ester, and combinations thereof;
   (ii) optionally heating the hair; and
   (iii) shaping the hair to a specific style.

2. The method of claim 1, wherein the disentangling agent is selected from the group consisting of 2-(2-aminoethoxy) ethanol, sodium dodecyl sulfate, dimethylacetamide, ethyl acetate, and mixtures of two or more thereof.

3. The method of claim 1, wherein the disentangling agent is 2-(2-aminoethoxy)ethanol.

4. The method of claim 1, wherein the disentangling agent is sodium dodecyl sulfate.

5. The method of claim 1, wherein the disentangling agent is dimethylacetamide.

6. The method of claim 1, wherein the disentangling agent is ethyl acetate.

7. The method of claim 1, wherein the solvent is water.

8. A method of styling hair, comprising:
   (i) contacting the hair with a first composition consisting of:
      (a) a reducing agent, wherein the reducing agent consists of cysteine;
      (b) one or more independently selected disentangling agents; and
      (c) a solvent selected from the group consisting of methanol, ethanol, isopropanol, and water;
         wherein each of the one or more independently selected disentangling agents is selected from the group consisting of an alkanolamine, an amine, an amide, an alcohol, an amino acid, a surfactant, an anhydride, a guanidinium salt, an ester, and combinations thereof;
   (ii) optionally heating the hair;
   (iii) shaping the hair to a specific style;
   (iv) contacting the hair with a second composition comprising:
      (c) one or more independently selected polycarboxylic acids;
      (d) one or more independently selected alkali metal hypophosphites; and
      (e) one or more independently selected crosslinking agents;
         wherein each of the one or more independently selected crosslinking agents is selected from the group consisting of a carbohydrate, an amino acid, a peptide, an oligopeptide, a protein hydrolysate, an alkanolamine, an alcohol, and combinations thereof; and
   (v) waiting a time sufficient to allow crosslinking.

9. The method of claim 8, wherein the disentangling agent is selected from the group consisting of 2-(2-aminoethoxy) ethanol, sodium dodecyl sulfate, dimethylacetamide, ethyl acetate, and mixtures of two or more thereof.

10. The method of claim 8, wherein the disentangling agent is 2-(2-aminoethoxy)ethanol.

11. The method of claim 8, wherein the disentangling agent is sodium dodecyl sulfate.

12. The method of claim 8, wherein the disentangling agent is dimethylacetamide.

13. The method of claim 8, wherein the disentangling agent is ethyl acetate.

14. The method of claim 8, wherein at least one of the one or more independently selected polycarboxylic acids in the second composition is citric acid.

15. The method of claim 8, wherein the second composition comprises:
  (i) from about 0.75 mol/L to about 1.2 mol/L citric acid;
  (ii) from about 0.75 mol/L to about 1.2 mol/L sodium hypophosphite; and
  (iii) from about 0.5 mol/L to about 1.1 mol/L of a crosslinking agent;
wherein the crosslinking agent is selected from the group consisting of 2-(2-aminoethoxy)ethanol, lysine, glycerol, and mannitol.

16. The method of claim 8, wherein the second composition comprises:
  (i) from about 0.75 mol/L to about 1.2 mol/L citric acid;
  (ii) from about 0.75 mol/L to about 1.2 mol/L sodium hypophosphite; and
  (iii) from about 0.5 mol/L to about 1.1 mol/L of a crosslinking agent;
wherein the crosslinking agent is 2-(2-aminoethoxy)ethanol.

17. The method of claim 8, wherein the second composition comprises:
  (i) from about 0.75 mol/L to about 1.2 mol/L citric acid;
  (ii) from about 0.75 mol/L to about 1.2 mol/L sodium hypophosphite; and
  (iii) from about 0.5 mol/L to about 1.1 mol/L of a crosslinking agent;
wherein the crosslinking agent is lysine.

18. The method of claim 8, wherein the second composition comprises:
  (i) from about 0.75 mol/L to about 1.2 mol/L citric acid;
  (ii) from about 0.75 mol/L to about 1.2 mol/L sodium hypophosphite; and
  (iii) from about 0.5 mol/L to about 1.1 mol/L of a crosslinking agent;
wherein the crosslinking agent is glycerol.

19. The method of claim 8, wherein the second composition comprises:
  (i) from about 0.75 mol/L to about 1.2 mol/L citric acid;
  (ii) from about 0.75 mol/L to about 1.2 mol/L sodium hypophosphite; and
  (iii) from about 0.5 mol/L to about 1.1 mol/L of a crosslinking agent;
wherein the crosslinking agent is mannitol.

20. The method of claim 8, wherein the solvent is water.

21. A method of styling hair, comprising:
  (i) contacting the hair with a first composition comprising:
    (a) a reducing agent, wherein the reducing agent consists of cysteine; and
    (b) a disentangling agent, wherein the disentangling agent consists of dimethylacetamide;
  (ii) optionally heating the hair; and
  (iii) shaping the hair to a specific style.

22. The method of claim 21, wherein the first composition further comprises a solvent.

23. A method of styling hair, comprising:
  (i) contacting the hair with a first composition comprising:
    (a) a reducing agent, wherein the reducing agent consists of cysteine; and
    (b) a disentangling agent, wherein the disentangling agent consists of dimethylacetamide;
  (ii) optionally heating the hair;
  (iii) shaping the hair to a specific style;
  (iv) contacting the hair with a second composition comprising:
    (c) one or more independently selected polycarboxylic acids;
    (d) one or more independently selected alkali metal hypophosphites; and
    (e) one or more independently selected crosslinking agents;
      wherein each of the one or more independently selected crosslinking agents is selected from the group consisting of a carbohydrate, an amino acid, a peptide, an oligopeptide, a protein hydrolysate, an alkanolamine, an alcohol, and combinations thereof; and
  (v) waiting a time sufficient to allow crosslinking.

24. The method of claim 23, wherein the first composition further comprises a solvent.

\* \* \* \* \*

UNITED STATES PATENT AND TRADEMARK OFFICE
CERTIFICATE OF CORRECTION

PATENT NO. : 10,828,246 B2
APPLICATION NO. : 15/284336
DATED : November 10, 2020
INVENTOR(S) : Yiqi Yang, Helan Xu and Kaili Song It is certified that error appears in the above-identified patent and that said Letters Patent is hereby corrected as shown below:

On the Title Page

In Item (56), Other Publications, Line 4, please delete "the the," and insert -- the --, therefor.

In the Specification

In Column 1, Line 8, please delete "Apr. 4," and insert -- Apr. 1, --, therefor.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*